(12) United States Patent
Carraway

(10) Patent No.: US 7,507,547 B2
(45) Date of Patent: Mar. 24, 2009

(54) SCREENING ASSAYS FOR ANTIOXIDANTS AND ANTIPROLIFERATIVE COMPOUNDS

(75) Inventor: Robert E. Carraway, Boston, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/223,395

(22) Filed: Sep. 9, 2005

(65) Prior Publication Data

US 2007/0231836 A1    Oct. 4, 2007

Related U.S. Application Data

(60) Provisional application No. 60/608,271, filed on Sep. 9, 2004.

(51) Int. Cl.
G01N 33/53 (2006.01)

(52) U.S. Cl. ...................................... 435/7.2

(58) Field of Classification Search ................ None
See application file for complete search history.

(56) References Cited

U.S. PATENT DOCUMENTS

| | | | |
|---|---|---|---|
| 5,204,354 A | 4/1993 | Chakravarty et al. |
| 5,250,558 A | 10/1993 | Chakravarty et al. |
| 5,407,916 A | 4/1995 | Wise et al. |
| 6,180,082 B1 | 1/2001 | Woltering et al. |
| 6,194,386 B1 | 2/2001 | Mertens et al. |
| 6,312,661 B1 | 11/2001 | Reubi |
| 6,630,123 B1 | 10/2003 | Woltering et al. |

OTHER PUBLICATIONS

Gully et al (1993, PNAS, 90:65-69).*
Seethalakshimi et al (1997, The Prostate, 31:183-192).*
Carraway et al (The Journal of Pharmacology and Experimental Therapeutics, Apr. 2004, 309(1):92-101).*
Adak et al., "Mechanism of horseradish peroxidase catalyzed epinephrine oxidation: obligatory role of endogenous $O_2$ and $H_2O_2$," Biochemistry, 37:16922-16933 (1998).
Babior et al., "Biological defense mechanisms. The production by leukocytes of superoxide, a potential bactericidal agent," J. Clin. Invest., 52:741-744 (1973).
Bartolini et al., "Retinoids and cancer: antitumor effect of ATRA and of a new derivative of retinoic acid, IIF, on colon carcinoma cell lines CaCo-2 and HT-29," Anticancer Res., 24:1779-1783 (2004).
Bass et al., "Flow cytometric studies of oxidative product formation by neutrophils: a graded response to membrane stimulation," J. Immunol., 130:1910-17 (1983).
Beaudet et al., "Internalization and intracellular mobilization of neurotensin in neuronal cells," Biochem. Pharmacol., 47:43-52 (1994).
Boudin et al., "Immunological recognition of different forms of the neurotensin receptor in transfected cells and rat brain," Biochem. J., 305:277-283 (1995).
Boveris A., "Determination of the production of superoxide radicals and hydrogen peroxide in mitochondria," Methods Enzymol., 105:429-435 (1984).

Brash, "Lipoxygenases: occurrence, functions, catalysis, and acquisition of substrate," J. Biol. Chem., 274:23679-82 (1999).
Carraway et al., "Effects of GTP analogs and metal ions on the binding of neurotensin to porcine brain membranes," Peptides, 14:37-45 (1993).
Carraway et al., "$Ca^{2+}$ channel blockers enhance neurotensin (NT) binding and inhibit NT-induced inositol phosphate formation in prostate cancer PC3 cells," J. Pharmacol. Exp. Ther., 307:640-650 (2003).
Carraway et al., "Polyphenolic antioxidants mimic the effects of 1,4-dihydropyridines on neurotensin receptor function in PC3 cells," J. Pharmacol. Exp. Ther., 309:92-101 (2004).
Carraway, et al. "Regulation of neurotensin receptor function by the arachidonic acid-lipoxygenase pathway in prostate cancer PC3 cells," Prostaglandins Leukot. Essent. Fatty Acids, 74(2):93-107 (2006).
Carraway and Leeman, "Structural requirements for the biological activity of neurotensin, a new vasoactive peptide," *Peptides: Chemistry, Structure and Biology*, Ann Arbor Science, pp. 679-685 (1975).
Carraway and Leeman, "Radioimmunoassay for neurotensin, a hypothalamic peptide," J. Biol. Chem., 251:7035-7044 (1976).
Casagrande and Darbon, "Effects of structurally related flavonoids on cell cycle progression of human melanoma cells: regulation of cyclin-dependent kinases CDK2 and CDK1," Biochem. Pharmacol., 61:1205-15 (2001).
Cochrane et al., "Mast cell histamine-releasing activities from stimulated rat neutrophils," Int. Arch. Allergy Appl. Immunol., 87(3):269-74 (1988).
Couder et al., "Synthesis and biological activities of psi ($CH_2NH$) pseudopeptide analogues of the C-terminal hexapeptide of neurotensin," Int. J. Pept. Protein Res., 41:181-84 (1993).
da Rocha et al., "Targeting protein kinase C: new therapeutic opportunities against high-grade malignant gliomas?" Oncologist, 7:17-33 (2002).
Diaz-Araya et al., "Antioxidant effects of 1,4-dihydropyridine and nitroso aryl derivatives on the $Fe^{+3}$/ascorbate-stimulated lipid peroxidation in rat brain slices," Gen. Pharmacol., 31:385-91 (1998).
Egli et al., "Organometallic $^{99m}Tc$-aquaion labels peptide to an unprecedented high specific activity," J. Nucl. Med., 40:1913-1917 (1999).
Faulkner and Fridovich, "Luminol and lucigenin as detectors for $O_2^-$," Free Radic. Biol. Med., 15:447-451 (1993).
Ferriola et al., "Protein kinase C inhibition by plant flavonoids: Kinetic mechanisms and structure-activity relationships," Biochem. Pharmacol., 38:1617-1624 (1989).
Fishman et al., "An agonist to the A3 adenosine receptor inhibits colon carcinoma growth in mice via modulation of GSK-3beta and NF-kappa B," Oncogene, 23:2465-2471 (2004).
Garcia-Garayoa et al., "Preclinical evaluation of a new, stabilized neurotensin(8-13) pseudopeptide radiolabeled with $^{99m}Tc$," J. Nucl. Med., 43:374-383 (2002).
Gopalakrishna and Gundimeda, "Antioxidant regulation of protein kinase C in cancer prevention," J. Nutr., 132:3819S-3823S (2002).
Gopalakrishna and Jaken, "Protein kinase C signaling and oxidative stress," Free Rad. Biol. Med., 28:1349-1361 (2000).
Granier et al., "Synthesis and characterization of neurotensin analogues for structure/activity relationship studies: Acetyl-neurotensin-(8-13) is the shortest analogue with full binding and pharmacological activities," Eur J. Biochem., 124: 117-124 (1982).

(Continued)

*Primary Examiner*—Sean E Aeder
(74) *Attorney, Agent, or Firm*—Fish & Richardson P.C.

(57) ABSTRACT

Provided are screening assays for identifying and evaluating compounds with antioxidant and/or antiproliferative activities.

16 Claims, 15 Drawing Sheets

OTHER PUBLICATIONS

Gully et al., "Biochemical and pharmacological activities of SR 142948A, a new potent neurotensin receptor antagonist," J. Pharmacol. Exper. Therap., 280:802-812 (1997).

Gully et al., "Biochemical and pharmacological profile of a potent and selective nonpeptide antagonist of the neurotensin receptor," Proc. Natl. Acad. Sci. USA, 90:65-69 (1993).

Hasegawa et al., "1-Methyl-4-phenylpyridinium ($MPP^+$) induces NADH-dependent superoxide formation and enhances NADH-dependent lipid peroxidation in bovine heart submitochondrial particles," Biochem. Biophys. Res. Commun., 170:1049-1055 (1990).

Hassan et al., "Involvement of MAP-kinase, PI3-kinase and EGF-receptor in the stimulatory effect of Neurotensin on DNA synthesis in PC3 cells," Regul. Pept., 120:155-166 (2004).

Hendriks et al., "Flavonoids inhibit myelin phagocytosis by macrophages; a structure-activity relationship study," Biochem. Pharmacol., 65:877-885 (2003).

Huang et al., "Effects of luteolin and quercetin, inhibitors of tyrosine kinase, on cell growth and metastasis-associated properties in A431 cells overexpressing epidermal growth factor receptor," Br. J. Pharmacol., 128:999-1010 (1999).

Hyslop and Sklar, "A quantitative fluorimetric assay for the determination of oxidant production by polymorphonuclear leukocytes: its use in the simultaneous fluorimetric assay of cellular activation processes," Anal. Biochem., 141:280-286 (1984).

Inoguchi et al., "Protein kinase C-dependent increase in reactive oxygen species (ROS) production in vascular tissues of diabetes: role of vascular NAD(P)H oxidase," J. Am. Soc. Nephrol., 14:S227-S232 (2003).

Isenberg et al., "Inhibition of WY-14,643 induced hepatic lesion growth in mice by rotenone," Carcinogenesis, 18:1511-1519 (1997).

Jager et al., "Blockage of intermediate-conductance $Ca^{2+}$-activated $K^+$ channels inhibit human pancreatic cancer cell growth in vitro," Mol. Pharmacol., 65:630-638 (2004).

Janero and Burghardt, "Antiperoxidant effects of dihydropyridine calcium antagonists," Biochem. Pharmacol., 38:4344-4348 (1989).

Jiang et al., "The inhibitory effects of gossypol on human prostate cancer cells-PC3 are associated with transforming growth factor $beta_1$ ($TGFbeta_1$) signal transduction pathway," Anticancer Res., 24:91-100 (2004).

Katsura et al., "Mechanism for increase in expression of cerebral diazepam binding inhibitor mRNA by nicotine: involvement of L-type voltage-dependent calcium channels," Mol. Brain Res. 80:132-141 (2000).

Keedwell et al., "An antagonist of retinoic acid receptors more effectively inhibits growth of human prostate cancer cells than normal prostate epithelium," Br. J. Cancer, 91:580-588 (2004).

Khaleghpour et al., "Involvement of the PI 3-kinase signaling pathway in progression of colon adenocarcinoma," Carcinogenesis, 25:241-248 (2004).

Knowles et al., "Flavonoids suppress androgen-independent human prostate tumor proliferation," Nutrition and Cancer, 38:116-122 (2000).

Korshunov et al., "High protonic potential actuates a mechanism of production of reactive oxygen species in mitochondria," FEBS Lett., 416:15-18 (1997).

Li et al., "Validation of lucigenin (bis-N-methylacridinium) as a chemilumigenic probe for detecting superoxide anion radical production by enzymatic and cellular systems," J. Biol. Chem., 273:2015-2023 (1998).

Li et al., "Trace determination of hydroxyl radical using fluorescence detection," Methods Enzymol., 300:202-216 (1999).

Lichtner et al., "Signaling-inactive epidermal growth factor receptor/ligand complexes in intact carcinoma cells by quinazoline tyrosine kinase inhibitors," Cancer Res., 61:5790-5795 (2001).

Liu et al., "Hypersensitization of tumor cells to glycolytic inhibitors," Biochemistry, 40:5542-5547 (2001).

Loprevite et al., "Pre-clinical evaluation of new antineoplastic agents in NSCLC cell lines: evidence of histological subtype-dependent cytotoxicity," Int. J. Oncol., 15(4):787-92 (1999).

Mak et al., "Protective effects of dihydropyridine Ca-blockers against endothelial cell oxidative injury due to combined nitric oxide and superoxide," Pharmacol. Res., 45:27-33 (2002).

Mason and Chester, "Diffusional dynamics of an active rhodamine-labeled 1,4-dihydropyridine in sarcolemmal lipid multibilayers," Biophys. J., 56:1193-1201 (1989).

Matsuyama et al., "Expression of lipoxygenase in human prostate cancer and growth reduction by its inhibitors," Int. J. Oncol., 24:821-827 (2004).

Mazella et al., "Solubilization and characterization of active neurotensin receptors from mouse brain," J. Biol. Chem., 263:144-49 (1988).

McLennan and Esposti, "The contribution of mitochondrial respiratory complexes to the production of reactive oxygen species," J. Bioenerg. Biomemb., 32:153-162 (2000).

Mitchell et al., "Antioxidant efficacy of phytoestrogens in chemical and biological model systems," Arch. Biochem. Biophys., 360:142-148 (1998).

Mo and Elson, "Studies of the isoprenoid-mediated inhibition of mevalonate synthesis applied to cancer chemotherapy and chemoprevention," Exp. Biol. Med., 229:567-585 (2004).

Mouria et al., "Food-derived polyphenols inhibit pancreatic cancer growth through mitochondrial cytochrome C release and apoptosis," Int. J. Cancer, 98:761-769 (2002).

Nakamura et al., "Role of reactive oxygen in tumor promotion: implication of superoxide anion in promotion of neoplastic transformation in JB-6 cells by TPA," Carcinogenesis, 6:229-235 (1985).

Nunez-Vergara et al., "Electrochemical and EPR characterization of 1,4-dihydropyridines. Reactivity towards alkyl radicals," Free Rad. Res., 37:109-120 (2003).

O'Prey et al., "Effects of dietary flavonoids on major signal transduction pathways in human epithelial cells," Biochem. Pharmacol., 66:2075-2088 (2003).

Ortiz et al., "Relative reactivity of dihydropyridine derivatives to electrogenerated superoxide ion in DMSO solutions: a voltammetric approach," Pharm. Res., 20:292-296 (2003).

Ozgova et al., "Different antioxidant effects of polyphenols on lipid peroxidation and hydroxyl radicals in the NADPH-, Fe-ascorbate- and Fe-microsomal systems," Biochem. Pharmacol., 66:1127-1137 (2003).

Rao et al., "Chemopreventive effect of farnesol and lanosterol on colon carcinogenesis," Cancer Detect. Prev., 26:419-425 (2002).

Rauen et al., "Hypothermia injury/cold-induced apoptosis—evidence of an increase in chelatable iron causing oxidative injury in spite of low $O_2^-/H_2O_2$ formation," FASEB J., 14:1953-1964 (2000).

Rice-Evans et al., "Structure-antioxidant activity relationships of flavonoids and phenolic acids," Free Radic. Biol. Med., 20(7):933-956 (1996).

Ruch et al., "Assay of $H_2O_2$ production by macrophages and neutrophils with homovanillic acid and horse-radish peroxidase," J. Immunol. Methods, 63(3):347-357 (1983).

Seethalakshmi et al., "Neurotensin receptor expression in prostate cancer cell line and growth effect of NT at physiological concentrations," The Prostate, 31(3):183-192 (1997).

Shukla and Gupta, "Molecular mechanisms for apigenin-induced cell-cycle arrest and apoptosis of hormone refractory human prostate carcinoma DU145 cells," Mol. Carcinog., 39(2):114-126 (2004).

Srinivasan et al., "Serum-stable neurotensin analogs as potential imaging and therapeutic agents for pancreatic cancer," J. Pept. Sci., 6:S184 (2000).

Staniek and Nohl, "$H_2O_2$ detection from intact mitochondria as a measure for one-electron reduction of dioxygen requires a non-invasive assay system," Biochim. Biophys. Acta, 1413(2):70-80 (1999).

Staniek and Nohl, "Are mitochondria a permanent source of reactive oxygen species?" Biochim. Biophys. Acta, 1460:268-275 (2000).

Valgimigli et al., "Measurement of oxidative stress by EPR radical-probe technique," Free Radic. Biol. Med., 31(6):708-716 (2001).

Vincent et al., "Neurotensin and neurotensin receptors," Trends Pharmacol. Sci., 20(7):302-309 (1999).

Xia et al., "Changes in the generation of reactive oxygen species and in mitochondrial membrane potential during apoptosis induced by the antidepressants imipramine, clomipramine, and citalopram and the effects on these changes by Bcl-2 and Bcl-$X_L$," Biochem. Pharmacol., 57(10):1199-1208 (1999).

Yoshida et al., "Antiproliferative effect of $Ca^{2+}$ channel blockers on human epidermoid carcinoma A431 cells," Eur. J. Pharmacol., 472:23-31 (2003).

Zheng et al., "Pharmacological, radioligand binding, and electrophysiological characteristics of FPL 64176, a novel nondihydropyridine $Ca^{2+}$ channel activator, in cardiac and vascular preparations," Mol. Pharmacol., 40(5):734-41 (1991).

Zsurger, et al., "Ontogenesis and binding properties of high-affinity neurotensin receptors in human brain," Brain Res., 586(2):303-10 (1992).

Carraway, R.E. and S. Hassan, "Neurotensin receptor binding and neurotensin-induced growth signaling in prostate cancer PC3 cells are sensitive to metabolic stress," Reg. Pept., 141(1-3):140-153 (2007).

Carraway, R.E. and S. Hassan, "Protein kinase C inhibitors alter neurotensin receptor binding and function in prostate cancer PC3 cells," Reg. Pept., 147(1-3):96-709(2008).

Elek et al., "Relevant genomics of neurotensin receptor in cancer," AntiCancer Res., 20:53-58 (2000).

Fischman et al., "A ticket to ride: peptide radiopharmaceuticals," J. Nucl. Med., 34:2253-2263 (1993).

Friry et al., "Production of recombinant large proneurotensin/neuromedin N-derived peptides and characterization of their binding and biological activity," Biochem. Biophys. Res. Commun., 290:1161-68 (2002).

Guha et al., "Neurotensin induces protein kinase C-dependent protein kinase D activation and DNA synthesis in human pancreatic carcinoma cell line PANC-1," Cancer Res., 62:1632-40 (2002).

Hassan, S. and R.E. Carraway, "Involvement of arachidonic acid metabolism and EGF receptor in neurotensin-induced prostate cancer PC3 cell growth," Regul. Pept., 133(1-3):105-114 (2006).

Ishizuka et al., "Neurotensin regulates growth of human pancreatic cancer," Ann. Surg., 217:439-446 (1993).

Maoret et al., "Neurotensin and a non-peptide neurotensin receptor antagonist control human colon cancer cell growth in cell culture and in cells xenografted into nude mice," Int. J. Cancer, 80:448-454 (1999).

Maoret et al., "Neurotensin receptor and its mRNA are expressed in many human colon cancer cell lines but not in normal colonic epithelium: binding studies and RT-PCR experiments," Biochem. Biophys. Res. Comm., 203:465-471 (1994).

Przedborski et al., "Neurotensin receptors in human meningiomas," Ann. Neurol., 30:650-654 (1991).

Reubi et al., "Neurotensin receptors in human neoplasms: high incidence in Ewing's sarcomas," Int. J. Cancer, 82:213-218 (1999).

Reubi et al., "Neurotensin receptors: a new marker for human ductal pancreatic adenocarcinoma," Gut, 42:546-550 (1998).

Reubi, J.C., "Regulatory peptide receptors as molecular targets for cancer diagnosis and therapy," Q. J. Nucl. Med., 41:63-70 (1997).

Sehgal et al., "Neurotensin is an autocrine trophic factor stimulated by androgen withdrawal in human prostate cancer," Proc. Nat'l. Acad. Sci. USA, 91:4673-4677 (1994).

Sethi et al., "Growth of small cell lung cancer cells: stimulation by multiple neuropeptides and inhibition by broad spectrum antagonists in vitro and in vivo," Cancer Res., 35:2737s-2742s (1992).

\* cited by examiner

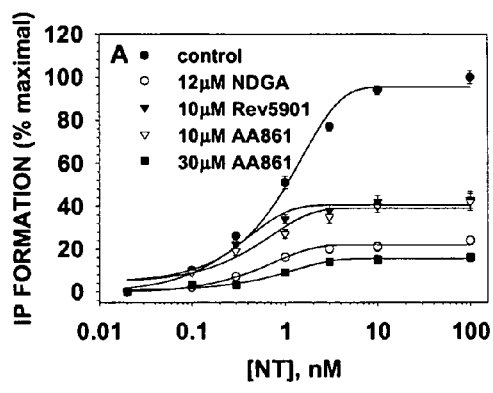
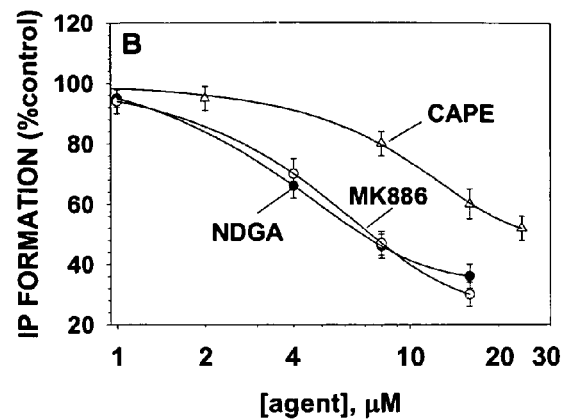
Fig. 15A
Fig. 15B
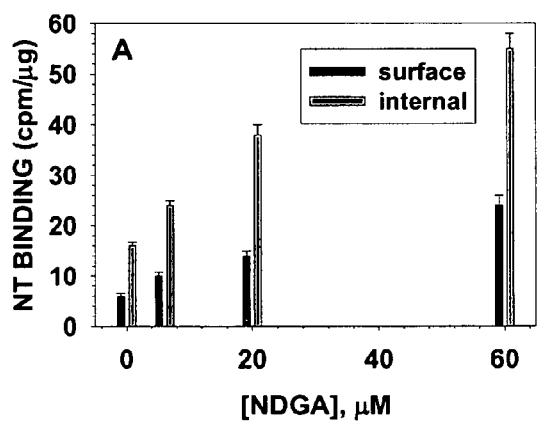
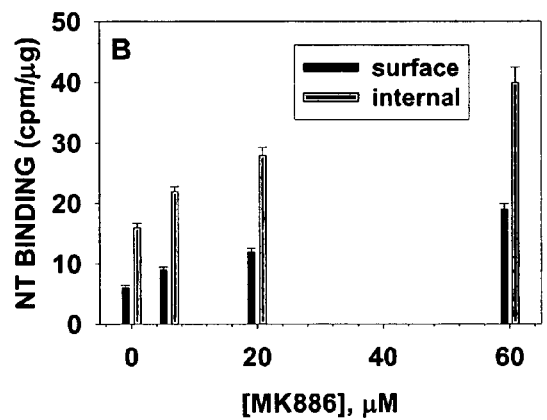
Fig. 16A
Fig. 16B

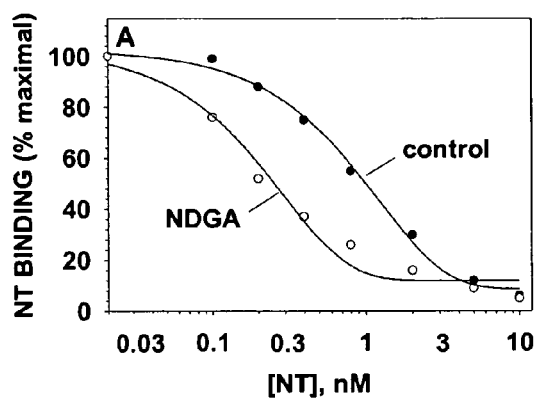 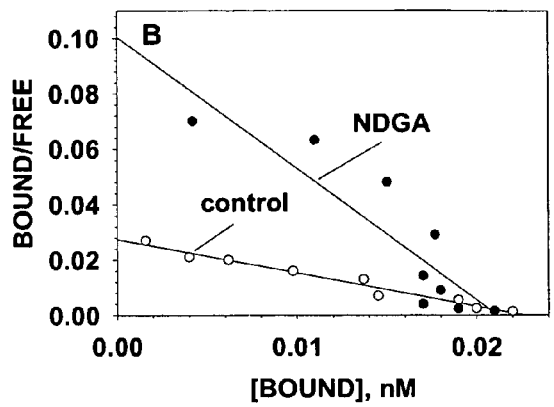
Fig. 17A
Fig. 17B
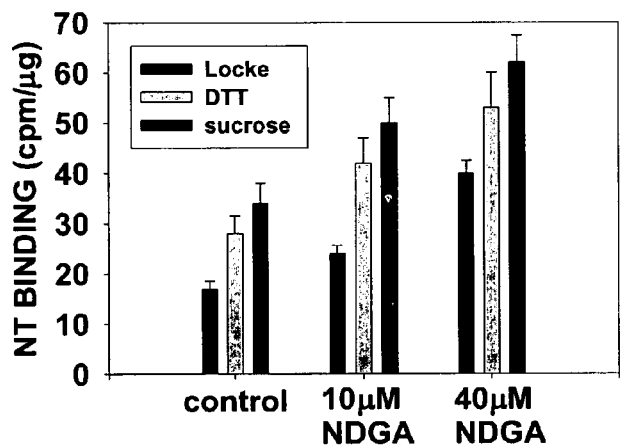
Fig. 18

SCREENING ASSAYS FOR ANTIOXIDANTS AND ANTIPROLIFERATIVE COMPOUNDS

CROSS-REFERENCE TO RELATED APPLICATIONS

This application claims the benefit of the filing date of U.S. Provisional Patent Application Ser. No. 60/608,271, filed on Sep. 9, 2004. The contents of this prior application are hereby incorporated by reference in their entirety.

GOVERNMENT FUNDING

This invention was made with government support under Department of Defense grant DAMD17-00-1-0528 and National Institute of Health center grant 5P30-DK32520. The government has certain rights in the invention.

TECHNICAL FIELD

This invention relates to methods of identifying compounds with antioxidant and antiproliferative activity.

BACKGROUND

The accumulation of reactive oxygen species (ROS) within cells can result in oxidative damage that is associated with the etiology or maintenance of many disease states. Disease states associated with ROS include, for example, cancer, diabetes, atherosclerosis, heart disease, Alzheimer's disease, and Parkinson's disease. An elevated level of ROS has been theorized to play a role in the development cancer by accelerating oxidative DNA damage. Consistent with a role for ROS in promoting cancer cell proliferation, certain antioxidants have been shown to inhibit cancer cell proliferation in several systems.

Neurotensin (NT) is a regulatory peptide that binds high-affinity neurotensin receptors (NTR) expressed in a variety of cells. NT binding to NTR alters intracellular inositol phosphate (IP) levels.

SUMMARY

The disclosed screening methods are based, in part, on the discovery that a subset of antioxidants, many of which have antiproliferative activity, can alter the ability of neurotensin (NT) to (i) bind to neurotensin receptors (NTR) and/or (ii) elevate the levels of intracellular inositol phosphates (IP). This discovery led to the recognition that (i) NT binding to NTR and (ii) NT-mediated IP formation can be used as readily detectable indicators of a selective antioxidant activity that relates to an anticancer action. These relationships are exploited in the screening assays described herein. These screening assays can (a) identify candidate antioxidant and/or antiproliferative compounds and (b) measure the relative antioxidant and/or antiproliferative potency and efficacy of compounds.

A significant advantage of many of the new screening assays described herein is that these assays can be used to identify compounds (i.e., candidate antioxidants or candidate antiproliferative compounds) according to their effect on living cells. Therefore, these assays selectively identify compounds that have a physiologically relevant antioxidant activity. The assays described herein are also inexpensive and simple to perform. In some cases the assays described herein can be performed in less than an hour. Furthermore, these assays can be readily scaled-up for high-throughput screening.

In one aspect, the new screens are used to monitor enhanced neurotensin receptor (NTR) ligand binding to identify candidate compounds with antioxidant and/or antiproliferative activity. In these screens, a cell expressing neurotensin receptors on its cell surface is contacted with (i) a test compound and (ii) an NTR ligand. Binding of the ligand to the cell is monitored. If the test compound enhances the binding of the ligand to the cell, relative to the binding of the ligand to a cell of the same cell type that is not contacted with the test compound, then the screen indicates that the test compound is a candidate compound with antioxidant and/or antiproliferative activity.

In a different aspect, the new screens described herein are used to monitor inositol phosphate (IP) formation within a cell to identify candidate compounds with antioxidant and/or antiproliferative activity. In these screens, one or more cells expressing neurotensin receptors on their cell surface are contacted with (i) a test compound and (ii) a neurotensin receptor (NTR) ligand. The level of IP formation within the cell is monitored. If the test compound inhibits IP formation in the cell (relative to IP formation in a cell of the same cell type that is contacted with the ligand, but is not contacted with the test compound) then the screen indicates that the test compound is a candidate compound that has antioxidant and/or antiproliferative activity.

The screens described herein can also be used to evaluate the antioxidant and/or antiproliferative efficacy of a test compound. For example, in screens that monitor the ability of a test compound to enhance NTR ligand binding to a cell, the level of enhanced ligand binding to the cell (relative to ligand binding to a cell of the same cell type that is not contacted with the test compound) can be used to assess the antioxidant and/or antiproliferative efficacy of the compound. In another example, in screens that monitor the ability of a test compound to inhibit IP formation in a cell, the level of reduced inositol phosphate formation within the cell (relative to inositol phosphate formation within a cell of the same cell type that is contacted with the neurotensin receptor ligand, but is not contacted with the test compound) can be used to assess the antioxidant and/or antiproliferative efficacy of the compound.

In some embodiments the screens described herein are adapted to high-throughput screening methods.

NTR ligands that can be used in the screens and methods described herein include, but are not limited to: neurotensin; neurotensin fragments such as neurotensin (8-13); neurotensin analogs or fragments thereof with a substitution at one or more of the following positions: Arg 8, Arg 9, Pro 10, Tyr 11, Ile 12, or Leu 13; highly substituted neurotensin analogs such as MP-2530; natural relatives of neurotensin such as Neuromedin-N, xenopsin, xenin, and histamine releasing peptide; and organomimics such as SR48692, SR142948A and levocabastine. In some embodiments, these NT receptor ligands are labeled.

Test compound that can be used in the screens and methods described herein include members of antioxidant classes such dihydropyridines, polyphenols, flavonoids, isoprenoids, retinoids, inhibitors of mitochondrial function, inhibitors of glycolysis, inhibitors of glycogen synthase kinase, inhibitors of flavoprotein oxidases, iron/zinc chelators, inhibitors of lipoxygenases, inhibitors of protein kinase C, inhibitors of PI3-kinase, inhibitors of tyrosine kinases, and estrogen agonists. Other test compounds include derivatives of antioxidants belonging to the aforementioned classes.

Cells that express NTR on their cell surface (and thus can be used in the screens and methods described herein) include tumor cells, e.g., cells from a Ewing's sarcoma, a myeloma, an astrocytoma, a lung tumor, a colon tumor, an ovarian tumor, a pancreatic tumor, or a prostate tumor.

An antioxidant, as used herein, is a compound that reduces the levels of reactive oxygen species (ROS) in a cell (e.g., by scavenging of ROS) and/or modulates the activity of a ROS-metabolizing pathway, for example, by reducing the activity of a ROS-generating pathway or increasing the activity of a ROS-consuming pathway.

As used herein, neurotensin (NT) refers to NT and NT analogs that bind to neurotensin receptors (NTR).

As used herein, inositol phosphate (IP) refers to the group of inositol phosphate containing compounds whose intracellular level increases in response to NT binding.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 15A is a graph showing NT-induced IP formation in the absence (control) or presence of indicated LOX inhibitors.

FIG. 15B is a graph showing that NT-induced IP formation is inhibited in a dose-responsive manner.

FIG. 16A is a graph showing that increasing concentrations of NDGA enhanced the amount labeled NT that bound (i) to cell surface and (ii) to internalized NTR receptors.

FIG. 16B is a graph showing that increasing concentrations of MK886 enhanced the amount labeled NT that bound (i) to cell surface and (ii) to internalized NTR receptors.

FIG. 17A is a graph showing the effect of NDGA on NT displacement as a percentage of maximal binding. The displacement curves indicate that NDGA enhanced NTR affinity, not NTR number.

FIG. 17B is a scatchard plot indicating that NDGA enhanced NTR affinity, not NTR number.

FIG. 18 is a graph that shows NDGA enhancement of NT binding in (i) Locke buffer, (ii) Locke+dithiothreitol (DTT), and (iii) Locke in which NaCl was replaced with sucrose.

DETAILED DESCRIPTION

The screening assays described herein provide methods for identifying compounds that have antioxidant activity and, in some cases, antiproliferative activity. Certain compounds with antiproliferative and/or antioxidant activity have been found to modulate neurotensin receptor (NTR) activity by (i) enhancing the ability of neurotensin (NT) to bind NTR on cell surfaces and/or (ii) inhibiting NT-mediated intracellular inositol phosphate (IP) production in cells. Thus, the assays disclosed herein use (i) enhanced NT-NTR binding and (ii) decreased IP production in cells as indicators that compounds have antioxidant and/or antiproliferative activity.

Compounds identified in the assays described herein are candidate compounds that can be used (i) to treat ROS-associated disorders and/or (ii) as lead compounds to develop related compounds that can be used to treat ROS-associated disorders, e.g., cancer. Other ROS-associated disorders include diabetes, atherosclerosis, heart disease, Alzheimer's disease, Parkinson's disease, chronic inflammation, chronic pain, skin disorders, and disorders associated with aging.

ROS, Cellular Proliferation, and NT Assays

The screens disclosed herein are based, in part, on the discovery that compounds with certain types of antioxidant activity affect the ability of NT (i) to bind NTR and (ii) to induce IP formation. As disclosed in the Examples below, NT-NTR binding and NT-mediated IP formation were modulated by a number of compounds that were either direct or indirect antioxidants. Direct antioxidants included polyphenols and flavonoids (e.g., resveratrol, quercetin, luteolin, and apigenin), as well as ROS-scavengers (e.g., dihydropyridines). Indirect antioxidants included flavoprotein oxidase inhibitors (e.g., diphenylene-iodonium), lipoxygenase inhibitors (nor-dihydroguaiaretic acid, MK886, retinoic acid, gossypol, Rev5901, AA861, ETYA, CAPE), inhibitors of mitochondrial oxidative metabolism (e.g., antimycin-A, rotenone, FCCP) and glycolytic inhibitors (e.g., 2-deoxyglucose). Other compounds that behaved as indirect antioxidants but acted by complex mechanisms included iron/zinc chelators (e.g., o-phenanthroline), protein kinase C inhibitors (e.g., bis-indoylmaleimide, rottlerin, Go-6983), and tyrosine kinase inhibitors (e.g., genistein, AG1478). Although these drugs may act via a variety of different pathways, they appear to share an ability to alter ROS in a manner affecting disease processes, and this ability can be rapidly assessed using the aforementioned assays for NT-binding and IP-formation in PC3 cells. See FIG. 20.

Figure 20:
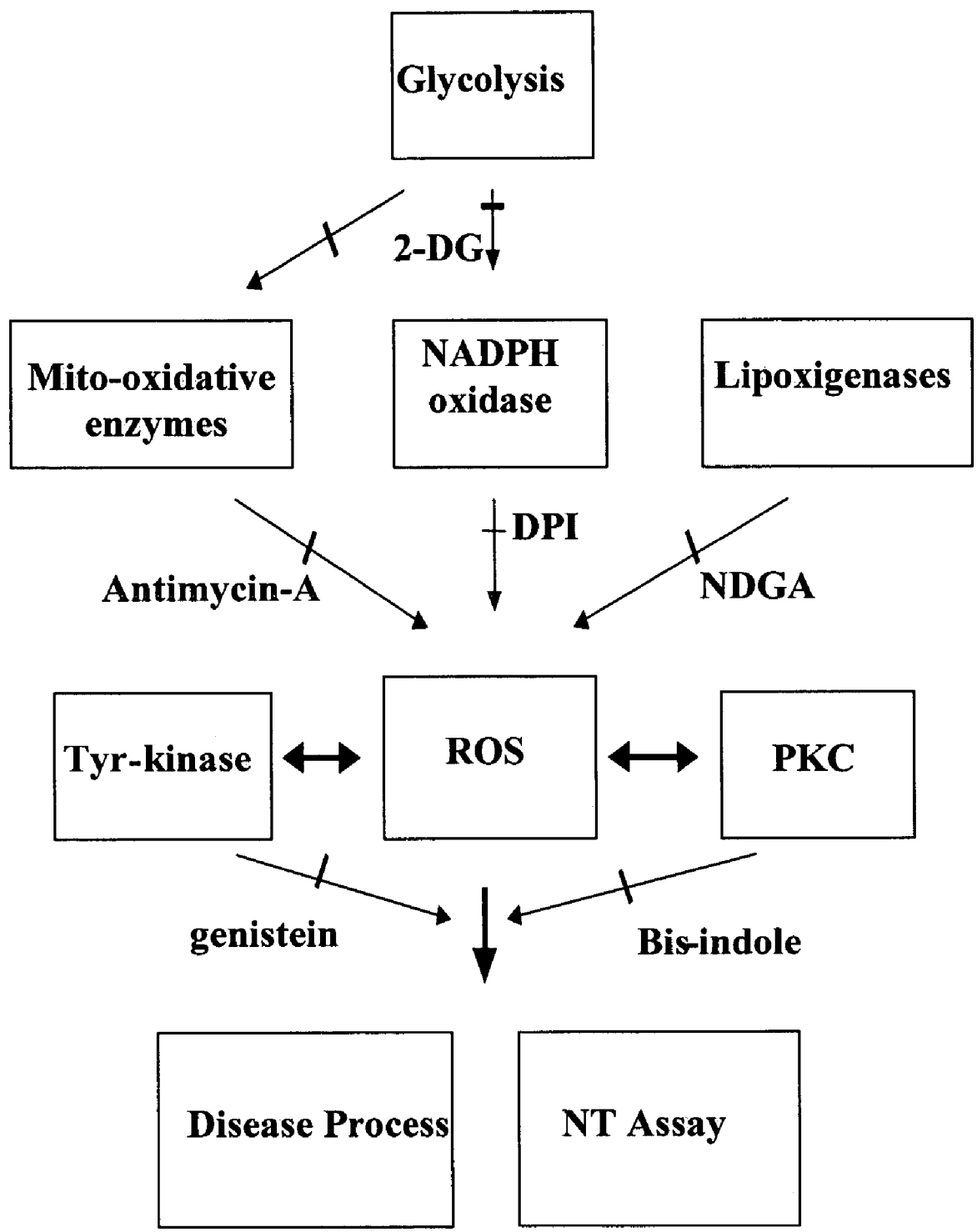
FIG. 20 is a schematic diagram of cellular pathways that (i) alter ROS levels in a cell, (ii) modulate NT-binding to NTR, (iii) modulate NT-mediated IP formation, and (iv) influence cellular proliferation. Some inhibitors of these pathways are also shown.

While not intending to be bound by a particular theory, FIG. 20 illustrates the relationships among various inputs that appear to determine cellular levels of ROS. Intracellular ROS levels ultimately impact a variety of disease processes and cause parallel changes in the NT assays disclosed herein. FIG. 20 depicts primary sources of ROS, such as mitochondrial oxidative enzymes, plasma membrane NADPH oxidases and lipoxygenases. ROS production by these systems may depend upon substrates derived from the glycolytic pathway and is intimately associated with the activation of tyrosine kinases and protein kinase C. A variety of the specific inhibitors of the pathways depicted in FIG. 20 also have antiproliferative activity.

The effectiveness of the presently disclosed assays to identify compounds with antioxidant and/or antiproliferative activity can be appreciated by noting the correlation between the NT-mediated effects (disclosed in the Examples below) of certain flavonoids and their documented ability to reduce ROS and inhibit cancer cell growth. The Examples below show that the efficacy order of flavonoids for altering NT binding to NTR was kaempferol>quercetin>luteolin≈apigenin>fiscetin≈genistein>myricetin >>catechin, taxifolin and rutin, (the last three were inactive).

The efficacy order to inhibit ROS formation for a group flavonoids has been found to be quercetin>luteolin>fiscetin>apigenin>morin, all of which were much more effective than epicatechin, which was inactive (Hendriks et al., *Biochem Pharmacol*, 65:877-885, 2003). The efficacy order to inhibit prostate cancer cell growth was quercetin>kaempferol>luteolin>apigenin>myricetin, all of which were much more effective than rutin, which was inactive (Knowles et al., *Nutrition and Cancer*, 38:116-122, 2000). The efficacy order to inhibit melanoma cell growth was luteolin>apigenin, all of which were much more effective than catechin and taxifolin, which were inactive (Casagrande and Darbon, *Biochem. Pharmacol.*, 61:1205-1215, 2001). The efficacy order to inhibit growth of cancers from skin, pancreas, liver and breast was luteolin and quercetin>>genistein>>taxifolin and catechin, (the last two were inactive) (Huang et al., *Brit. J. Pharmacol.*, 128:999-1010, 1999). The efficacy order to inhibit protein kinase C was quercetin>phloretin>apigenin>>catechin and taxifolin, (the last two were inactive)(Ferriola et al., *Biochem. Pharmacol.*, 38:1617-1624, 1989). Interestingly, flavonoids could have multiple inputs into the scheme of FIG. 20, since they are known PKC inhibitors and have an ability to scavenge lipid peroxides and ROS. In addition, their structural resemblance to ubiquinol suggests that they could interact with flavoprotein oxidases involved in ROS production.

The general agreement amongst these results of the assays disclosed herein and previously disclosed antioxidant/antiproliferative activity is apparent. The agreement suggests that similar chemical features are required for (i) the effects on NT, (ii) the effects on ROS formation and (iii) cancer cell growth. However, a compound with an antiproliferative effect detected by the new methods need not rely on a reduction in ROS formation. It is conceivable that a compound detected by the new methods may exert an antiproliferative effect by increasing ROS.

Libraries of Test Compounds

The new methods can be used to identify compounds, e.g., small organic or inorganic molecules (molecular weight less than 1,000 Da), oligopeptides, oligonucleotides, or carbohydrates, that (i) increase NT binding to NTR and/or (ii) reduce NT-mediated biosynthesis of an intracellular inositol phosphate (IP) pool. In certain embodiments, screens of the present invention utilize libraries of test compounds. As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). A test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include antioxidants, compounds that structurally resemble antioxidants, peptides, peptidomimetics (e.g., peptoids), amino acids, amino acid analogs, polynucleotides, polynucleotide analogs, nucleotides, nucleotide analogs, and organic or inorganic compounds (e.g., heteroorganic or organometallic compounds).

Test compounds can be screened individually or in parallel. An example of parallel screening is a high throughput drug screen of large libraries of chemicals. Such libraries of test compounds can be generated or purchased, e.g., from Chembridge Corp., San Diego, Calif. Libraries can be designed to cover a diverse range of compounds. For example, a library can include 500, 1000, 10,000, 50,000, or 100,000 or more unique compounds. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., Gordon et al., *J. Med. Chem.*, 37:1385-1401, (1994); DeWitt, and Czarnik, *Acc. Chem. Res.*, 29:114, (1996); Armstrong, et al., *Acc. Chem. Res.*, 29:123, (1996); Ellman, J. A. *Acc. Chem. Res.*, 29:132, (1996); Gordon, et al., *Acc. Chem. Res.*, 29:144 (1996); Lowe, G. *Chem. Soc. Rev.*, 309 (1995); Blondelle et al. *Trends Anal. Chem.*, 14:83 (1995); Chen, et al., *J. Am. Chem. Soc.*, 116:2661 (1994); U.S. Pat. Nos. 5,359,115, 5,362,899, and 5,288,514; and PCT Publication Nos. WO92/10092, WO93/09668, WO91/07087, WO93/20242, and WO94/08051).

Libraries of compounds can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky, *Principles of Peptide Synthesis*, 2nd ed., Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of Hobbs DeWitt et al. (*Proc. Natl. Acad. Sci. USA*, 90:6909 (1993)). Other synthesis methods, including the "tea-bag" technique of Houghten (see, e.g., Houghten et al., *Nature*, 354:84-86 (1991)) can also be used to synthesize libraries of compounds according to the subject invention.

Libraries of compounds can be screened to determine whether any members of the library have a desired activity and, if so, to identify the active species. Methods of screening combinatorial libraries have been described (see, e.g., Gordon et al., *J Med. Chem.*, supra). After screening, compounds that have a desired activity can be identified by any number of techniques (e.g., mass spectrometry (MS), nuclear magnetic resonance (NMR), matrix-assisted laser desorption ionisation/time of flight (MALDI-TOF) analysis, and the like). Exemplary assays useful for screening libraries of test compounds are described herein.

Screening Methods

The invention provides methods for identifying candidate compounds with antioxidant and/or antiproliferative activities. Although applicants do not intend to be bound by any particular theory as to the biological mechanism involved, such compounds are thought to modulate the metabolism of reactive oxygen species (ROS) and thereby alter (i) NTR-ligand binding to NTR and (ii) NTR ligand-mediated intracellular IP formation. Regardless of the mechanisms involved, the disclosed screening assays are useful for the evaluation of antioxidant and/or antiproliferative activities that correlate with (i) enhanced NTR ligand binding to NTR and (ii) diminished NTR ligand-mediated intracellular IP production.

1. Candidate Compounds that Enhance NTR-ligand Binding to NTR

In certain aspects, screening for candidate compounds with antioxidant and/or antiproliferative activity is accomplished by identifying from a group of test compounds those that enhance the ability of NTR ligand to bind to NTR expressed by a cell or tissue. NTR may be any of a number of NTR subtypes or other receptors that bind NT. At this time, three NTR subtypes have been identified (NTR1, NTR2 and NTR3), the first two of which are G-protein-coupled receptors (GPCRs) and the third of which is sortilin (Vincent et al., *Trends Pharmacol. Sci.*, 20:302-309, 1999). The presently disclosed screening assays measure enhanced NT binding to NTR both on the cell surface and/or NT binding to internalized NTR. Test compounds that enhance the ability of NTR ligand to bind to NTR are referred to herein as "candidate compounds."

In one aspect, enhanced binding of NTR ligand to NTR is detected, for example, by plating NTR-expressing cells in multi-well (e.g., 12-, 48-, 96-, 384-, 1536-well or higher) microtiter plate(s). A test compound and NT peptide, e.g., labeled NT peptide, are then added to the plate. NT is allowed to bind to NTR, e.g., for 30 minutes at 37° C. The binding reaction can be stopped, e.g., by placing cells on ice. Cells are washed, and the amount of NT that binds to the cells can be measured. The amount of NT that binds a cell contacted with a test compound is compared to the amount of NT that binds a cell that has not been contacted with a test compound, e.g., a cell that was contacted with (a) NT alone or (b) NT and a compound that is known not to enhance NT binding to NTR on cells.

Enhanced binding of NT to NTR can be detected by incubating tissue slices with labeled NT in the presence of candidate compounds. If the labeled NT is radioactive, binding can be measured autoradiographically or by scintillation. Other labels, such as fluorescent groups, enzymes, etc., could also be used with appropriate methods of detection, as explained below.

NT binding to NTR can be detected by any of a variety of methods. For example, NT can be labeled (e.g., with a radioisotope, fluorophore, chromophore, or the like), and after allowing NT to bind NTR, the amount of label bound to NTR can be detected. Labeled NT can also be produced as a fusion protein with a protein label that can be detected optically, e.g., a green fluorescent protein (which can be detected under UV light). Labeled NT, as used herein, can also include NT produced as a fusion protein with an enzyme having a detectable enzymatic activity, such as horseradish peroxidase, alkaline phosphatase, β-galactosidase, or glucose oxidase. In this embodiment, labeled NT bound to NTR is detected by contacting NTR with substrate for the NT fusion protein's enzymatic activity, and measuring production of detetable enzyme product associated with NTR. Genes encoding all of these enzymes have been cloned and are available for use by skilled practitioners. If desired, labeled NT can include an antigen, which can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins). An antibody that specifically binds to NT can be used in an immunoassay to detect NT bound to NTR. If desired, the antibody can be labeled (e.g., fluorescently or with a radioisotope) and detected directly (see, e.g., West and McMahon, *J. Cell Biol.*, 74:264, 1977). Alternatively, a second antibody can be used for detection (e.g., a labeled antibody that binds to the Fc portion of the anti-NT antibody.

In some embodiments, specific binding of NT to NTR is detected by including an amount of unlabeled NT with an amount of labeled NT. In these screens, different groups of cells expressing NTR are each contacted with a test compound and a differing ratio of labeled NT to unlabeled NT. Binding displacements curves and binding parameters can be determined using methods known in the art (See, e.g., Cheng and Prusoff, *Biochem. Pharmacol.*, 22:3099-3108, 1973).

In certain other embodiments, the interaction of NT and NTR is detected by fluorescence resonance energy transfer (FRET) between a donor fluorophore covalently linked to NT (e.g., a fluorescent group chemically conjugated to NT, or a variant of green fluorescent protein (GFP) expressed as an NT-GFP chimeric protein) and an acceptor fluorophore covalently linked to NTR, where there is suitable overlap of the donor emission spectrum and the acceptor excitation spectrum to give efficient nonradiative energy transfer when the fluorophores are brought into close proximity through the protein-protein interaction of NT and NTR. In other embodiments, the protein-protein interaction is detected by reconstituting domains of an enzyme, e.g., beta-galactosidase (see Rossi et al., *Proc. Natl. Acad. Sci. USA*, 94:8405-8410 (1997)).

Methods described herein can be used for high throughput screening of numerous test compounds to identify candidate compounds. By high-throughput screening, it is meant that the method can be used to screen a large number of candidate compounds relatively easily and quickly. For example, cells expressing NTR are contacted with NT and a plurality of test compounds. The plurality of test compounds can be contacted to the cells in groups or separately. In certain embodiments, cells expressing NTR are contacted with each test compound of a plurality separately, e.g., only one compound is placed in each well of a multiwell plate(s). In one embodiment, the method can screen libraries of test compounds. Libraries of test compounds are discussed in detail above. Libraries can include, e.g., antioxidants, compounds that are structurally similar to known antioxidants, natural and synthetic products, including combinatorial chemistry products, synthetic and natural peptides, recombinant or natural proteins, nucleic acids, carbohydrates etc. Typically, the libraries are in a form compatible with screening in multiwell plates (e.g., 96, or higher, well plates). The assay is particularly useful for automated execution in a multiwell format in which many of the steps are controlled by computer and carried out by robotic equipment (e.g., Asset™ system, from The Automation Partnership Ltd., Hertfordshire, UK).

2. Candidate Compounds that Inhibit NT-induced Inositol Phosphate Formation

In certain aspects, screening of test compounds is accomplished by identifying from a group of test compounds those that inhibit NTR ligand-mediated formation of inositol phosphate (IP) in a cell. Test compounds that inhibit NTR ligand-mediated formation of inositol phosphate (IP) in a cell are also referred to herein as "candidate compounds."

In one aspect, test compounds that inhibit NTR ligand-mediated IP formation are detected by plating NTR-expressing cells in multi-well (e.g., 96-well or higher) microtiter plate(s). Cells are incubated with a compound that can be used to monitor IP formation in a cell (i.e., an IP-labeling compound). Examples of IP-labeling compounds include radiolabeled inositol or radioisotopes (such as phosphate, carbon, or hydrogen) suitable for incorporation into newly synthesized IP in a cell. A test compound and NT peptide are added to the plate. After a time that allows for NT-induced expansion of an intracellular IP pool, e.g., 30 minutes at 37° C., the reaction is stopped in a manner that protects the IP pool, e.g., by replacing cell media with ice-cold formic acid in methanol. Plates can be stored overnight. IP levels in the cells are measured. Detecting inhibition of NT-induced IP formation in cells contacted with a test compound involves measuring a difference in IP levels between (1) cells contacted with both a test compound and NT and (2) cells that contacted with (a) NT alone or (b) NT and a compound known not to affect NT-mediated IP formation in cells.

Compounds suitable for monitoring IP formation in a cell include agents suitable for labeling inositol phosphate molecules. For example, radionucleotides such as $^{32}P$, $^{33}P$, $^{3}H$, and $^{14}C$ can be incorporated into IP molecules during NT-mediated IP formation thereby allowing for radiodetection of newly formed IP molecules. Radiolabels can be incorporated into an IP precursor, e.g., an inositol molecule, and the IP precursor can be used as a compound suitable for monitoring IP formation in the assays described herein. Commercially manufactured labeled IP precursors (e.g., labeled myo-Inositol) can also be used in the screening assays described herein.

Measurement of IP levels can be performed in many ways. IPs can be extracted from cells using an acid solution. Optionally, cellular protein and lipid debris are separated from IPs, e.g., by centrifugation/precipitation of cell debris or by organic extraction. In some assays fractions containing IPs can then be bound to an anion-exchange resin (by mixing with anion-exchange beads or loading the samples onto a column). The resin can be washed and IPs eluted. Eluted IPs are then detected using techniques appropriate to the detection of the IP-labeling compound, e.g., radiometric assays.

3. Neurotensin Receptor Ligands: NT, NT Derivatives, and Other NTR Ligands

An exemplary NTR ligand for use in the assays described herein is neurotensin, a thirteen amino acid peptide with the following amino acid sequence: pGlu-Leu-Tyr-Glu-Asn-Lys-Pro-Arg-Arg-Pro-Tyr-Ile-Leu (SEQ ID NO:1). Neurotensin, sometimes referred to as NT (1-13), has a Kd of about 0.3 nM for binding to membranes containing the neurotensin-1 receptor (NTR1) and about 2-6 nM for binding to the neurotensin-2 receptor (NTR2) (Zsurger et al., *Brain Res.*, 586:303, 1992). The C-terminal six residues of NT are most essential for binding to receptors and for biologic activity (Carraway et al., Peptides: Chemistry, Structure and Biology, Ann Arbor Science, pp. 679-685, 1975). Consequently, natural relatives and synthetic, analogs of NT containing these six residues or similar substitutions can be ligands for NTR. Amino acids with similar properties can be substituted at some of the six C-terminal positions (e.g., Lys for Arg, Trp for Tyr, Leu for Ile, Val for Leu), yielding NT derivatives with some ability to bind NTR. Such derivatives can be NTR ligands for the assays described herein.

Thus, a number of NT derivatives, e.g., NT fragments, NT relatives and NT analogs that bind NTR can be used instead of NT in the screening assays described herein. NT derivatives include peptides containing a reversed N-terminal to C-terminal amino acid sequence of NT. NT peptide can be modified by substituting one or more amino acids in the peptide with an artificial amino acid analog. For example, NT derivatives can include one or more D-amino acids substituted for the corresponding one or more L-amino acids of NT. In other NT derivatives, substituted artificial amino acid analogs include β-amino acids, β-substituted β-amino acids ("β³-amino acids"), phosphorous analogs of amino acids, such as α-amino phosphonic acids and α-amino phosphinic acids, and amino acids having non-peptide linkages. Artificial amino acids can be used to create peptidomimetics, such as peptoid oligomers (e.g., peptoid amide or ester analogs), β-peptides, cyclic peptides, oligourea or oligocarbamate peptides; or heterocyclic ring molecules.

As the positions Arg 8-Arg 9 and Tyr 11-Ile 12 in NT are known to be susceptible to endopeptidases, these peptide bonds can be altered to stabilize an NTR ligand. For example, a number of NT derivatives in which these peptide bonds have been systematically reduced are described in Couder et al., *Int. J. Pept. Protein Res.*, 41:181, (1993). One NTR derivative is Trp 11 NT(1-13), a peptide that is identical to NT (1-13) except for the substitution of tryptophan for tyrosine at amino acid 11; Trp 11 NT(1-13) shows a binding affinity of about 1 nM for the neurotensin-1 receptor and about 27 nM for the neurotensin-2 receptor. Another NT derivative, called MP-2530, contains the following substitutions: Ile 12 to t-buGly, Arg 8 to (PipAm)Gly, and Lys 6 to (Pip)Gly. MP-2530 demonstrated increased serum and urine stability while retaining NTR binding affinity. Srinivasan et al., *J. Pept. Sci.*, 6:S184, 2000. Other stabilized NT analogs have been described in Eglio et al., *J. Nucl. Med.*, 40:1913-1917, 1999.

NTR ligands also include NT derivatives that are fragments of NT or extended forms of NT that retain the ability to bind NTR. One example of an NT fragment that binds to NTR is neurotensin (8-13), with the sequence Arg-Arg-Pro-Tyr-Ile-Leu (SEQ ID NO:2), described by Granier et al., *Eur J. Biochem.*, 124:117-124 (1982). NTR ligands also include NT fragment derivatives, such as the stabilized neurotensin (8-13) pseudopeptide described by García-Garayoa et al., *J. Nucl. Med.*, 43:374-383 (2002). Still other NT fragment derivatives that bind NTR are described in U.S. Pat. No. 6,194,386. NTR ligands include naturally occurring NT-like peptides such as neuromedin-N (Lys-Ile-Pro-Tyr-Ile-Leu (SEQ ID NO:3)), xenopsin (pGlu-Gly Lys-Arg-Pro-Trp-Ile-Leu (SEQ ID NO:4)), xenopsin-related peptide (Phe-His Pro Lys-Arg Pro-Trp-Ile-Leu (SEQ ID NO:5)), histamine releasing peptide (Ile-Ala-Arg-Arg-His Pro-Tyr-Phe-Leu (SEQ ID NO:6)), and derivatives thereof.

NT ligands also include organomimics that exhibit specific binding to NT receptors. Organomimics can be produced by and selected from combinatorial chemistry libraries using NTR binding assays. Such compounds are useful in the assays described herein. Some NT ligands that are organomimics have been described: SR48692, a selective antagonist for the neurotensin-1 receptor, has the chemical structure: {2-[1-(7-chloro-4-quinolinyl)-5-(2,6-dimethoxyphenyl) pyrazol-3-yl) carboxylamino]tricyclo (3.3.1.1.$^{3.7}$) decan-2-carboxylic acid} (Gully et al., *Proc. Natl. Acad. Sci. USA*, 90:65, 1993). SR142948A, a non-selective antagonist that binds to both neurotensin-1 and neurotensin-2 receptors, has the chemical structure: 2-(5,6-dimethylaminopropyl)-1-[4-{N-(3-dimethylaminopropyl)-N-methylcarba-moyl}-2-isopropylphenyl]-1H-pyrazole-3-carbonyl)aminoadamantane-2-carboxylic acid (Gully et al., *J. Pharmacol. Exper. Therap.*, 280:802, 1997). It is conceivable that other organomimics will be found that bind to NTR. Levocabastine is another organic compound that has no obvious structural similarity to NT but is able to bind to NTR, specifically to NTR2. U.S. Pat. Nos. 5,250,558 and 5,204,354 disclose Neurotensin receptor antagonists. U.S. Pat. No. 5,407,916 discloses peptidic Neurotensin agonists.

Further Testing of Candidate Compounds

Candidate compounds can optionally be further tested to determine if they have (a) antioxidant activity and/or (b) antiproliferative activity. Candidate compounds that have antioxidant activity are referred to herein as antioxidant agents. Candidate compounds with antiproliferative activity are referred to herein as antiproliferative agents. Tests for antioxidant activity or antiproliferative activity may be carried out in whole cell preparations and/or in ex vivo cell-free systems.

Antioxidant Activity Assays

Testing of a candidate compound for antioxidant activity can be accomplished by means known to those in the art. Generally, a candidate compound is contacted to a reactive oxygen species-producing system, e.g., a cell, a mitochondrial preparation, or an in vitro reconstitution of a ROS-metabolizing pathway. ROS levels or the activity of a ROS-metabolizing pathway is measured. If the compound decreases ROS levels then the compound is an antioxidant agent. If the compound modulates the activity of a ROS metabolizing pathway in a way that decreases intracellular levels of ROS, then the compound is an antioxidant agent.

There are numerous direct and indirect ways of measuring ROS levels in a cell or in a reconstitution assay in vitro. For example, spectrophotometric assays measure the change in absorption characteristics of chromogens after interaction with ROS. Some assays use the reduction of tetrazolium salts to formazan (Rauen et al., *J FASEB*, 14:1953-1964 (2000)) or the reduction of ferricytochrome C (Babior et al., *J. Clin. Invest.*, 52:741-744 (1973). Other chromogens used are epinephrine (Adak et al., *Biochemistry*, 37:16922-16933, (1998) and Boveris A., *Methods Enzymol.*, 105:429-435, (1984)) or adrenaline (Hasegawa, *Biochem. Biophys. Res. Commun.*, 170:1049-1055, (1990)).

Fluorescence assays can be used measure the change in fluorescence properties of probes in response to oxidation by ROS. Some assays use heme peroxidase to catalyze ROS-dependent dimerization of substituted phenolic compounds. For example, p-hydroxyphenylacetate (PHPA) (Hyslop and Sklar, *Anal. Biochem.*, 141:280-286, (1984) or homovanillic acid (Ruch et al., *J. Immunol. Methods*, 63:347-357, (1983) are substrates that can be used with horseradish peroxidase in specific and sensitive assays for $H_2O_2$ determination. Scopoletin is a fluorescent compound that becomes non-fluorescent in the presence of horseradish peroxidase and ROS (Korshunov, et al., *FEBS Lett.*, 416:15-18, 1997). Variations of these assays reduce signal interference due to mitochondrial constituents (Staniek and Nohl, *Biochim. Biophys. Acta*, 1413:70-80, 1999 and Staniek and Nohl, *Biochim. Biophys. Acta*, 1460:268-275, 2000).

Hydroethidine (HET), a specific indicator of ROS (i.e., superoxide), has been shown to be specifically oxidized to fluorescent ethidium (Xia et al., *Biochem. Pharmacol.*, 57:1199-1208, 1999). Fluorescent methods to detect hydroxyl radicals, in some cases involve the separation of fluorescent radicals by high-performance liquid chromatography (Li et al., *Methods Enzymol.*, 300:202-216, 1999). A widespread method of detecting intracellular ROS uses the low fluorescence probe 2',7'-dichlorodihydrofluorescin (DCFH) diacetate. This probe is oxidized by ROS (i.e., hydrogen peroxide) to yield 2',7'-dichlorofluorescin (DCF) diacetate, which is highly fluorescent and can be quantified by fluorescence imaging (Bass et al., *J. Immunol.*, 130:1910-17, 1983).

Another technique for the direct detection of free radicals uses electron paramagnetic resonance (EPR) spectroscopy. See, e.g., Valgimigli et al., *Free Radic. Biol. Med.*, 31:708-716, (2001). Relatively low sensitivity can be compensated by "spin-trapping" stable radical compounds that accumulate until detectable. Nitrones and nitroso compounds are classical spin-traps, producing, in the presence of $O_2$.- or OH.- specific nitroxyl radicals.

Chemiluminescent substrates such as luminol and lucigenin can be used to detect the energy transfer between molecules during redox reactions, e.g., in cellular systems. Reaction with a ROS causes the substrates to form an unstable intermediate that luminesces during decomposition to ground state (Faulkner et al., *Free Radic. Biol. Med.*, 15:447-451 (1993)). These substrates can be extremely sensitive and have been used to measure ROS in intact cells and isolated mitochondria (Li et al., *J. Biol. Chem.*, 273:2015-2023 (1998)).

Some antioxidant assays test the ability of a candidate compound to reduce ROS production via specific metabolic pathway. For example, a candidate compound can be tested for any of the following activities: glycolytic inhibition, mitochondrial inhibition, lipoxygenase inhibition, flavoprotein oxidase inhibition, iron/zinc chelation, ROS scavenging, protein kinase-c inhibition, tyrosine kinase inhibition. Although these activities affect a number of different pathways, they share an ability to alter ROS.

Additionally, candidate compounds can be tested in animal models of ROS-related disorders, e.g., cancer, diabetes, atherosclerosis, heart disease, Alzheimer's disease, Parkinson's disease, chronic inflammation, chronic pain, skin disorders, and disorders associated with aging. Such animal models are known in the art.

Assays of Antiproliferative Activity

1. Cell-based Proliferation Assays

Cell-based proliferation assays can be used to confirm the antiproliferative activity of a candidate compound. Generally, the assays include contacting a candidate compound to proliferating cells, e.g., lung, colon, ovary, pancreas, breast, or prostate cancer cells (cancer cell lines are known in the art, and many are available from depositories such as American Type Culture Collection (Manassas, Va.)), and subsequently assaying the effect of the candidate compound on proliferation of the cells. A candidate compound is an antiproliferative agent if the compound reduces proliferation of the cells, relative to similar cells that are not exposed to the candidate compound.

A number of proliferation assays are based on the incorporation of labeled nucleotide or nucleotide analogs into the DNA of proliferating cells. In these assays cells are exposed to a candidate compound and to a labeled nucleotide, e.g., $^{14}C$-thymidine, $^3H$-thymidine, or 5-bromo-2-deoxyuridine (BrdU). Proliferation is quantified by measuring the amount of labeled nucleotide taken up by the cells. Radiolabeled nucleotides can be measured by radiodetection methods; antibodies can be used to detect incorporation of BrdU. Other assays rely on the conversion of chemical precursors to a dye in dividing cells. Some assays measure the conversions of tetrazolium salts (e.g., methyl thiazole tetrazolium (MTT), 2-(4-Iodophenyl)-3-(4-nitrophenyl)-5-(2,4-disulfophenyl)-2H-tetrazolium (WST-1), or 3'-{1-[(phenylamino)-carbonyl]-3,4-tetrazolium}-bis(4-methoxy-6-nitro) benzene-sulfonic acid hydrate (XTT)) to formazan by cellular mitochondrial dehydrogenases. Mitochondrial dehydrogenase activity increases in proliferating cells, thereby increasing the amount of formazan dye. The amount of formazan dye measured by absorbance is an indication of proliferation. Still other assays measure cellular proliferation as a function of ATP production. For example, the luciferase enzyme catalyzes a bioluminescent reaction using the substrate luciferin. The amount of bioluminescence produced by a sample of cells measures the amount of ATP present in the sample, which is an indicator of the number of cells.

Some cell proliferation assays directly measure the number of cells produced by a number of founder cells in the presence of a candidate compound. For example, soft-agar colony formation assays, cancer cells are suspended in agar-containing nutrient containing medium. Cells are incubated under conditions that allow for cell proliferation in the absence of a candidate compound. Colonies that form, if any, are stained with dye, e.g., crystal violet, and counted.

2. In Vivo Proliferation Assays

Candidate compounds can also be further tested for the ability to prevent proliferation of cancer cells in vivo. Generally, these assays involve administering a candidate compound to an animal model of cancer. The proliferation of cancer cells in the animal model is assessed. A candidate compound that reduces proliferation of cancer cells in the animal, relative to the proliferation of cancer cells in a control that has not been exposed to a candidate compound, is an antiproliferative agent.

In some assays, a candidate compound is administered to a xenograft animal model. In these assays, cancer tissue is transplanted into animals, e.g., immune-deficient mice. One or more test animals are treated with a pharmaceutical composition that includes a candidate compound. One or more control animals are treated with a pharmaceutical composition lacking the candidate compound. The proliferation of cancer tissues (e.g., by measuring tumor size, tumor volume, and/or tumor weight) in the two sets of animals is assessed. If a candidate compound reduces the amount of proliferation in one or more test animals, relative to control animals, then it is a candidate compound.

Other types of animal models can be used instead of a xenograft model. For example, antiproliferative activity can be evaluated using transgenic animal models that inducibly produce tumors. In some of these models, an inducible protein activates a proto-oncogene or inactivates a tumor suppressor gene, thereby bringing about uncontrolled cellular proliferation. Some transgenic models have been developed that produce tumor formation in particular tissues, e.g., breast or prostate tissues. Candidate compounds can also be tested in animal models that have a very high incidence of cancer, e.g., a dog model of prostate cancer. In still other animal models, a chemical carcinogen is administered to an animal to induce tumor formation.

The antiproliferative activity of a candidate compound can be evaluated in any animal model of cancer described herein, as well as in others known in the art, to further determine if the compound is an antiproliferative agent.

Medicinal Chemistry

Once candidate compounds, including candidate compounds that are antioxidant agents and/or antiproliferative agents have been identified, the compounds can be formulated for the treatment of diseases associated with ROS, e.g., cancer, or standard principles of medicinal chemistry can be used to produce derivatives of the compound for the treatment of diseases associated with ROS, e.g., cancer.

A candidate compound that has positive in vivo results is a candidate therapeutic agent. Candidate therapeutic agents can be optimized, derivatized, or made into pharmaceutical composition for clinical trials. Candidate therapeutic agents effective in clinical trials are therapeutic agents for treatment of ROS-associated disorders.

Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al., *J. Antibiot.*, 41:1430-8 (1988). Furthermore, if the biochemical target of the compound (or agent) is known or determined, the structure of the target and the compound can inform the design and optimization of derivatives. Molecular modeling software is commercially available (e.g., from Molecular Simulations, Inc.) for this purpose.

Pharmaceutical Compositions

Candidate compounds, and/or derivatives thereof, can be incorporated into pharmaceutical compositions. Pharmaceutical compositions typically include a candidate compound, or a derivative thereof, and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (e.g., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™ EL (BASF, Parsippany, N.J.) or phosphate buffered saline (PBS). In all cases, the composition should be sterile and fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be achieved by including an agent which delays absorption, e.g., aluminum monostearate or gelatin, in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches, and the like can contain any of the following ingredients or compounds of a similar nature: a binder such as microcrystalline cellulose, gum tragacanth, or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active compound(s) are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compound(s) can also be prepared in the form of suppositories (e.g., with conventional suppository bases such as cocoa butter and other glycerides) or retention enemas for rectal delivery.

In one embodiment, the active compound(s) are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., bone or cartilage, in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of an active compound can include a single treatment (e.g., for imaging) or, preferably, can include a series of treatments. Appropriate doses of the compound depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration. For example, pharmaceutical composition that includes one or more compound of interest can be packaged together with a pharmaceutical composition that includes an antioxidant. Such packaging makes administration of the combination therapies disclosed herein.

The invention is further described in the following examples, which do not limit the scope of the invention described in the claims.

EXAMPLES

Example 1

Iodination of Ligands and Binding to PC3 Cells

[$^{125}$I]-sodium iodide (2000 Ci/mmol), was obtained from Dupont New England Nuclear (Boston, Mass.). [4-azido-Phe$^6$]-NT was synthesized using reagents from Novabiochem (San Diego, Calif.). Chemicals whose origin is unspecified were obtained from Sigma (St. Louis, Mo.).

Ligands were iodinated using the following concentrations: 3 nmol for human epidermal growth factor (EGF) obtained from Calbiochem, San Diego, Calif.; 15 nmol each for neurotensin (NT), (Tyr 4, Nle 14)-bombesin, pindolol, and des-Gly-[Phaal, D-Tyr(Et)2, Lys6, Arg8]-vasopressin (HOLVA) obtained from Peninsula, Belmont, Calif. Iodinations were performed using chloramine T (10 μg) as described (Carraway et al., *Peptides*, 14:37-45, 1993). All reactions were stopped using sodium metabisulfite (30 μg), except for EGF (stopped by dilution). The mono-iodinated products were purified by reverse-phase HPLC using µBondapak™ C18 (3.9×300 mm column; Millipore, Bedford, USA) eluted at 1.5 ml/minute with a linear gradient (60 minutes) from 0.1% trifluoroacetic acid (TFA) to 60% $CH_3CN$, 0.1% TFA. The specific activity of the purified $^{125}$I-NT was 1000-2000 cpm/fmol as determined by radioimmunoassay (Carraway et al., *J. Biol. Chem.*, 251:7035-7044, 1976).

PC3 cells were obtained from American Type Culture Collection (Manassas, Va.) and maintained as described (Seethalakshmi et al., *The Prostate*, 31:183-192, 1997). Cells, passaged no more than 30 times, were grown to 95% confluency in 24-well culture plates. For binding studies, cells were washed with 2 ml/well of Hepes-buffered Locke-BSA (Locke): 148 mm NaCl, 5.6 mM KCl, 6.3 mM Hepes, 2.4 mM $NaHCO_3$, 1.0 mM $CaCl_2$, 0.8 mM $MgCl_2$, 5.6 mM glucose, and 0.1% bovine serum albumin (BSA); pH 7.4. Equilibrium binding at 37° C. was performed for 25 minutes using $10^5$ cpm/ml of each $^{125}$I-labeled ligand in 1.0 ml Locke with varying amounts of unlabeled ligand (0-1 µM). The reaction was stopped on ice for 15 minutes, the medium was aspirated and the cells were washed twice with 2 ml and once with 4 ml ice-cold saline. During this 5 minute washing procedure, dissociation of $^{125}$I-NT from cell receptors was <1%. Total cellular binding was assessed by measuring radioactivity and protein (Bio-Rad assay; BSA standard) in cells extracted in 0.6 ml 0.2M NaOH. A Packard 10-well γ-counter was used to measure radioactivity. Specific binding was defined as that displaceable by 1 mM ligand. Binding displacement curves were constructed for each set of treatments and binding parameters were determined by Scatchard analysis. Ki was determined by using the equation {Ki=IC50/1+[L]/Kd} where Kd and [L] are the dissociation constant and the concentration of the ligand, respectively (Cheng and Prusoff, *Biochem. Pharmacol.*, 22:3099-3108, 1973).

Specific binding of $^{125}$I-NT ($10^5$ cpm/ml) to PC3 cells at 37° C. was >95% of total binding and was 16.8±0.81 cpm $^{125}$I-NT bound/mg protein (n=12), which corresponded to ~3000 cpm $^{125}$I-NT bound/well. Table 1 gives the binding parameters determined for NT binding to PC3 cells. The data show that labeled ligand, e.g., $^{125}$I-NT, remained intact during incubation and that dissociation did not occur during washing.

TABLE 1

Parameters Determined for Binding of $^{125}$I-labeled Ligands to PC3 Cells

| Ligand [a] | Specific Binding [b] (% of total) | Bmax [c] (fmol/mg) | Ki [c] (nM) |
|---|---|---|---|
| $^{125}$I-NT | 95 | 158 ± 9 | 1.0 ± 0.07 |
| $^{125}$I-[Nle$^{14}$]-bombesin | 95 | 1016 ± 64 | 0.6 ± 0.09 |
| $^{125}$I-EGF | 95 | 151 ± 11 | 0.6 ± 0.07 |
| $^{125}$I-pindolol | 66 | 86 ± 6 | 0.3 ± 0.05 |
| $^{125}$I-HOLVA | 77 | 156 ± 12 | 0.5 ± 0.07 |

[a] NT, [Nle$^{14}$]-bombesin and EGF are agonists for NTR1, bombesin receptor and EGF receptor, respectively. Pindolol and HOLVA are antagonists for β2-adrenergic receptor and vasopressin (V1a) receptor, respectively.
[b] All ligands were HPLC purified (specific activity, >1000 Ci/mmol). Specific binding was measured to near confluent cells (≈185 µg protein/well) using $10^5$ cpm $^{125}$I-ligand in 1.0 ml Locke (see Methods).
[c] Scatchard analysis was performed using 12 ligand concentrations and results were from 3 to 9 experiments.

Example 2

Calcium Channel Blockers (CCBs) Enhance NT Binding to PC3 Cells

Phloretin was obtained from Calbiochem (San Diego, Calif.). Nimodipine, verapamil, diltiazem, NT, nifedipine (NIF), miconazole, tetraethylammonium (TEA), flunarizine, phenylarsine oxide, amiloride, pindolol were from Sigma (St. Louis, Mo.). Stocks of test agents were prepared daily (10 mM in DMSO) and diluted into Locke just before use, except for SKF-96365, miconazole, and trifluoperazine, which were dissolved in Locke. Binding experiments were performed as described in Example 1.

Figure 1A:
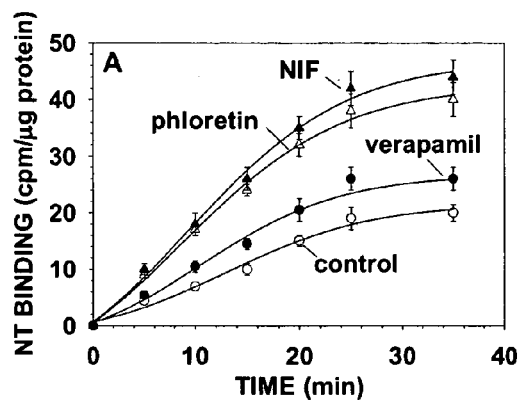
FIG. 1A is a graph comparing the effect of several dihydropyridines (DHPs) on steady state binding of NT to PC3 cells.
Figure 1B:
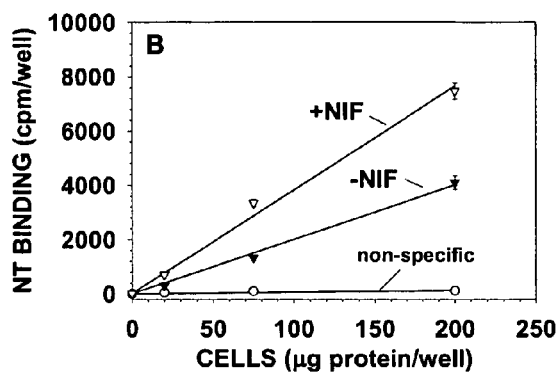
FIG. 1B is a graph showing that Nifedipine (NIF) enhanced specific binding of NT to PC3 cells, but did not affect non-specific binding.
Figure 1C:
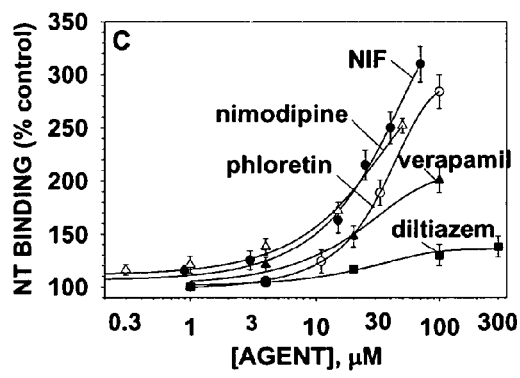
FIG. 1C is a graph showing the relative efficacy of several DHPs for enhancing NT binding.
Figure 1D:
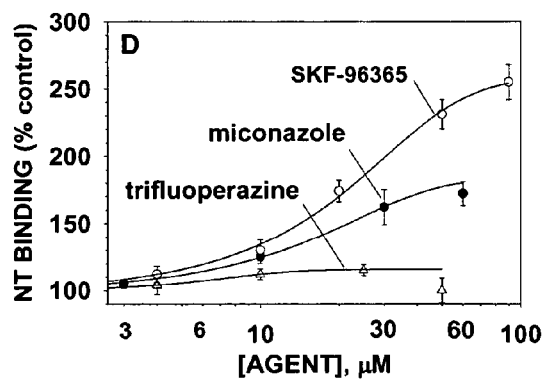
FIG. 1D is a graph comparing the ability of store-operated (SKF-96365, miconazole) and non-specific (trifluoperazine) calcium channel blockers (CCBs) to enhance NT binding.

Calcium channel Blockers (CCBs) include blockers of voltage gated calcium channel (VGCC) and store-operated calcium channels (SOCC). VGCC blockers NIF, phloretin, and verapamil were found to increase the apparent rate of and the steady state level of NT binding to PC3 cells (FIG. 1A). NIF enhanced specific binding, without altering non-specific binding and was effective across a 10-fold range in cell density (FIG. 1B). The order of efficacy was NIF>phloretin>verapamil>diltiazem. NT binding was increased as much as 3.1-fold by NIF, 2.9-fold by phloretin, 2.0-fold by verapamil and 1.4-fold by diltiazem (FIG. 1C). A sub-class of VGCC blockers referred to as 1,4-dihydropyridines (DHPs), represented here by nifedipine (NIF) and nimodipine (NIM), were the most potent agents, elevating NT binding at sub-micromolar concentrations {control, 100±4%; 0.3 mM NIM, 116±5% (p<0.05); 0.9 mM NIF, 115±5% (p<0.05)}. Whereas less specific CCBs (flunarizine, tetrandrine, trifluoperazine, and chlorpromazine) had only modest effects (Table 2), well-defined blockers of SOCC (SKF-96365, miconazole) enhanced NT-binding up to 2.9-fold (FIG. 1D; Table 2). The data showed that certain CCBs, including DHPs and some SOCC blockers, enhanced NT-binding.

TABLE 2

Activity of CCBs on NT Binding and NT-induced IP Formation

| | | NT Binding [a] | | IP Formation [b] | |
|---|---|---|---|---|---|
| Channel | Agent | Efficacy (% increase) | EC50 (µM) | Efficacy (% decrease) | IC50 (µm) |
| VGCC | NIF [c] | 210 | 15 | 74 | 15 |
| | Phloretin [c] | 186 | 27 | 70 | 23 |
| | Verapamil [c] | 85 | 43 | 58 | 53 |
| | Diltiazem [c] | 38 | >300 | nd | nd |
| | flunarizine [d] | 45 | >100 | nd | nd |
| | tetrandrine [d] | 35 | >100 | nd | nd |
| SOCC | SKF-96365 | 155 | 23 | 69 | 26 |
| | miconazole | 75 | 60 | 54 | 51 |
| | trifluoperazine | 16 | >100 | 14 | >100 |
| | chlorpromazine | 36 | >100 | nd | nd |

[a] Efficacy was defined as the maximal % increase in NT binding observed for each agent. ED50 was defined as the [agent] at which NT binding was increased by 80%. The data are means determined in 3-8 experiments for each agent.
[b] Efficacy was defined as the maximal % decrease in NT-induced IP formation observed for each agent. IC50 was defined as the [agent] at which IP formation was decreased by 50%. The data are means determined in 3 to 8 experiments for each agent. nd, not determined.
[c] L-type CCBs.
[d] L-type/T-type blockers.

Example 3

CCBs Inhibited NT-induced IP Formation in PC3 Cells

[1,2-$^3$H(N)]-myo-inositol (60 mCi/mmol) was obtained from Dupont New England Nuclear (Boston, Mass.). IP formation was measured using [$^3$H]-inositol to label the phosphoinositide pool as described in Chen and Chen, *Endocrinology*, 140:1639-48 (1999). PC3 cells in 24-well plates were incubated 48 hours with myo-[$^3$H]-inositol (2.5 mCi/ml) in medium 199, 5% fetal calf serum. Medium 199 (Difco, Franklin Lakes, N.J.) was chosen because of its low inositol content. After washing with 2 ml Locke, cells were preincubated 10 minutes with test agents in Locke, 15 mm LiCl, and reactions were started by adding a maximal dose of NT (30 nM) or vehicle. After 30 minutes at 37° C., medium was aspirated, ice-cold 0.1 M formic acid in methanol (1 ml) was added and plates were placed at −20° C. overnight. Samples were transferred to tubes using two 2 ml water washes and [$^3$H]-IP was adsorbed to 0.25 ml AG1×8 slurry (formate was from Bio-Rad, Hercules, Calif.), which washed five times in 5 mM myo-inositol (5 ml) and eluted in 0.75 ml 1.5 M ammonium formate, 0.1 M formic acid. Scintillation counting was performed on 0.5 ml eluate in 5 ml Ecoscint™ (National Diagnostics, Atlanta, Ga.).

Figure 2A:
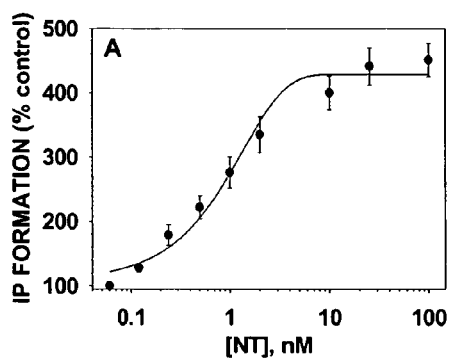
FIG. 2A is a graph showing NT-induced inositol phosphate (IP) formation in PC3 cells.
Figure 2B:
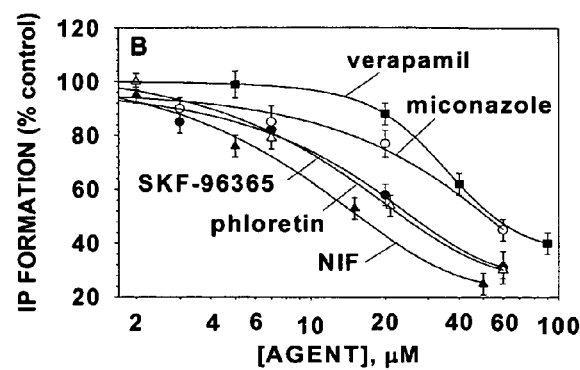
FIG. 2B is a graph showing that DHPs inhibited NT-induced IP formation in PC3 cells.

NT increased IP formation ≅5-fold in PC3 cells with an EC50≅1 nM as shown in FIG. 2A. VGCC blockers inhibited the response to a maximal dose of NT as shown in FIG. 2B, with an efficacy order (NIF>phloretin>verapamil) similar to that for enhancement of NT binding (Table 2). SOCC blockers also inhibited the response to NT (FIG. 2B), giving an efficacy order (SKF-96365>miconazole>trifluoperazine) similar to that for enhancing NT binding (Table 2). For each of these agents, the EC50 for enhancing NT binding was similar to the IC50 for inhibiting NT-induced IP formation (Table 2), and there was a strong statistical correlation ($r^2$=0.842). Enhanced NT-binding and decreased IP formation appear to be linked, e.g., one effect could have caused the other. The results indicated that the effects of CCBs on NT binding and NT-induced IP formation have a similar chemical sensitivity. The results also showed that inhibited intracellular IP formation can be used to identify antioxidants. Although the responses in the two NT assays were correlated, it still was not clear whether these effects depended on the ability of CCBs to block calcium entry into the cells or if some other property of these compounds brought about the effects.

Example 4

CCBs Enhanced Photoaffinity Labeling of NTR1 in PC3 Cells

To demonstrate the involvement of NT receptors in the enhanced cellular binding of NT, we measured the effects of CCBs on the labeling of NTR1 isolated by specific immunoprecipitation. The labeled proteins were also identified by western blotting.

For immunoblots, PC3 cells in 60 mm dishes were washed in Locke-containing protease inhibitors: 0.5 mm EDTA, 0.5 µM PMSF, 0.5 µM TPCK and 0.5 µM o-phenanthroline. Protease inhibitors and chemicals whose source is not indicated were obtained from Sigma. Cells were lysed in 100 µl of 2×sodium dodecyl sulfate (SDS) loading buffer with inhibitors, scraped into microfuge tubes and sonicated (20 seconds) on ice. Membranes were isolated from regions of adult rat brains (Carraway et al., *Peptides*, 14:37-45, 1993) and P2 pellets were extracted in 2×SDS loading buffer and sonicated. Cell and tissue extracts were boiled 5 minutes and separated by SDS-PAGE on 10% polyacrylamide minigels. Proteins were electroeluted onto PVDF membranes (Immobilon™ P, Millipore). After blocking in 5% non-fat milk in TTBS: 0.05% Tween™ 20, 20 mM Tris, 0.5 M NaCl, for 1 hour and washing 3 times with TTBS, blots were incubated with the primary antiserum (1:1000) in blocking buffer for 18 hours at 4° C. Our rabbit antiserum (Ab-NTR1) was raised using a synthetic peptide corresponding to residues 398-418 of human NTR1 conjugated to keyhole limpet hemocyanin. The antibodies were affinity purified before use. Blots were washed in TTBS, then incubated with horseradish peroxidase-linked goat anti-rabbit antibody (1:1000) for 1 hour at 20° C., and washed again in TTBS. Enhanced chemiluminescence was performed according to the manufacturer's instructions (Santa Cruz). After stripping (1 hour at 70° C. in 62.5 mM Tris-HCl, 2% SDS, 0.1 M β-mercaptoethanol, pH 6.8) and washing in TBS, blots were reprobed with antigen-adsorbed antisera to validate the results.

For UV crosslinking, [4-azido-Phe$^6$]-NT was iodinated and purified by HPLC to ≅1500 Ci/mmol. PC3 cells in 10 cm dishes were incubated with 0.3×10$^6$ cpm/ml $^{125}$I-[4-azido-Phe$^6$]-NT in 8 ml Locke, 25 minutes at 37° C., in presence and absence of Ca$^{2+}$-channel agents. 1 µM NT was added to controls. Cells were placed on ice for 30 minutes, irradiated at 254 nm with a handheld UV light for 5 minutes at 3 cm, washed in ice-cold phosphate-buffered saline (PBS) and lysed in 10 mM Hepes, 1 mM EDTA, 0.5 mM o-phenanthroline, phenylmethyl sulfonylfluoride (PMSF), and tosyl-phenylalanine chloromethyl ketone (TPCK) (pH 7.4). Membranes, collected by centrifugation (at 30,000 g, 20 minutes) were solubilized in 250 µl 50 mm Tris buffer (pH 7.4), 150 mM NaCl, 0.5% Triton™ X-100, 0.5% NP-40, 5% glycerol at 4° C. for 2 hours. Solubilized NTR1, diluted 2-fold in buffer without detergent, was immunoprecipitated by addition of our rabbit antiserum (Ab-NTR1) (final 1:100). During western blotting, Ab-NTR1 detected two major bands in extracts of PC3 cells, the parent protein of 50 kDa and a breakdown product of 33 kDa, similar to results observed in other cells (Boudin et al., *Biochem. J.*, 305:277-83, 1995). After 18 hours at 4° C., protein A-agarose (10 mg, Sigma) was added for 6 hours. After agarose beads were washed three times with PBS at 4° C., associated radioactivity was measured using a γ-counter. Usually the immunoprecipitate contained ≅5% of the solubilized cpm for samples prepared in the absence of NT. SDS-PAGE was used in some cases to validate that the radiolabeled material represented NTR1. For this, the beads were boiled 5 minutes in an equal volume of 2×SDS sample buffer and extracts were subjected to SDS-PAGE using 10% polyacrylamide gels, followed by autoradiography.

Figure 3A:
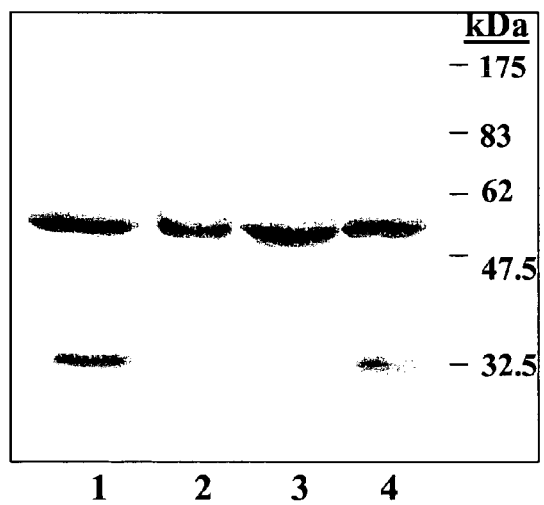
FIG. 3A is an image of an immunoblot that used the anti-NTR1 antibody described herein to western blot for NTR1 in rat brain extracts.
Figure 3B:
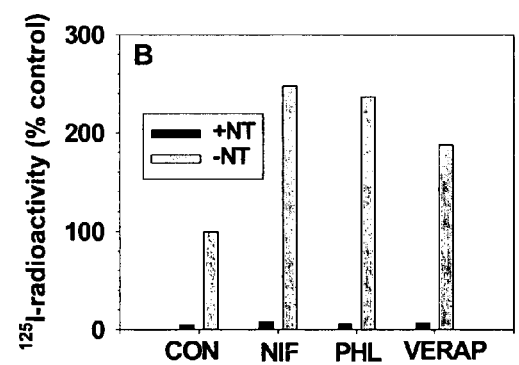
FIG. 3B is a chart showing that CCBs enhanced cross-linking of radiolabeled NT into NTR1, as assessed by immunoprecipitation.
Figure 5A:
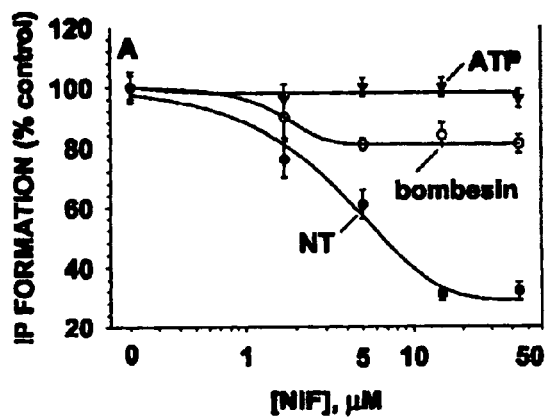
FIG. 5A is a chart showing that pretreatment of cells with NIF inhibited NT-mediated IP formation by ~69%, whereas NIF inhibited bombesin-mediated IP formation by only ~19%, and ATP-induced IP formation was not affected by NIF.
Figure 5B:
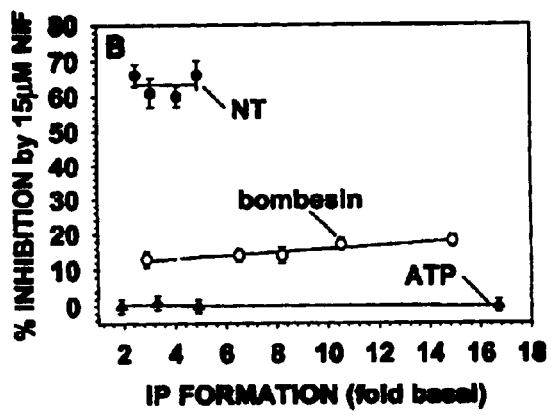
FIG. 5B is a chart showing the inhibitory effect of 15 μM NIF on NT-, bombesin-, and ATP-induced IP formation in PC3 cells as a percent of IP formation over basal IP levels.

NTR1 is a 46 kDa protein that has been immunologically characterized and labeled using UV-activatable cross linkers (Mazella et al., *J. Biol. Chem.*, 263:144-49, 1988). Initially, we used western blotting to verify the specificity of our antiserum (Ab-NTR1) raised towards the C-terminus of human NTR1. Whereas extracts of rat brain gave a single band at ≅50 kDa, PC3 cells gave this parent protein, along with a 33 kDa fragment (FIG. 3A), in keeping with published results (Boudin et al., *Biochem. J.*, 305:277-283, 1995). Next, we used UV-light to incorporate $^{125}$I-(4-azido-Phe$^6$)-NT into PC3 cells treated with CCBs or control, and we assessed the incorporation of radioactivity into immunoprecipitated NTR1. The results in FIG. 5B showed that the radioactivity associated with NTR1 was enhanced by NIF (2.8 fold; p<0.001), phloretin (1.8 fold; p<0.05) and verapamil (1.5 fold; p<0.05) as compared to the control. For each agent, the increase in immunoprecipitated radioactivity (FIG. 3B) was similar to the increase in NT-binding to PC3 cells seen at the appropriate dose (See FIG. 1C). SDS-PAGE and autoradiography on selected samples verified the presence of 50 kDa and 33 kDa radiolabeled proteins (data not shown). These results indicate that the CCBs shown to enhance NT binding did so by increasing the association of $^{125}$I-NT with NTR1.

Example 5

CCBs Had an Indirect Action on NTR1

Since there was precedent in the literature for tyrosine kinase inhibitors acting directly on the EGFR to elevate its binding (Lichtner et al., *Cancer Res.*, 61:5790-5795, 2001), we tested whether CCBs would directly affect the binding of $^{125}$I-NT to isolated PC3 cell membranes in vitro. PC3 cell membranes were prepared and collected by centrifugation at 30,000 g (Seethalakshmi et al., *The Prostate*, 31:183-192, 1997). Binding of $^{125}$I-NT ($10^5$ cpm) to membranes (10-50 µg) was performed at 20° C. for 60 minutes in 10 mM Tris-HCl (pH 7.5), containing 1 mM $MgCl_2$, 1 mM dithiothreitol (DTT), 0.1% BSA and protease inhibitors as described. Membranes were collected and washed onto glass fiber (GF-B) filters using a Brandel cell harvester, and the filters were counted using a γ-counter (Carraway et al., *Peptides*, 14:37-45, 1993).

NT binding to cell membranes was not increased by NIF, phloretin, or verapamil (Table 3), indicating that these agents were unable to act directly on NTR1. Although a key participant in the reaction might have been lost during membrane isolation, it seems more likely that there was a requirement for cellular metabolism and/or architecture. Thus, the increase in NT binding observed in live cells most likely reflected an indirect effect of CCBs, possibly by way of an effect on cellular enzymes or metabolism.

TABLE 3

Effects of Ca $^{2+}$-Channel Blockers on NT-binding to PC3 Cell Membranes

| Agent[a] | Specific NT-Binding (% control) at Dose of Agent[b] | | | |
|---|---|---|---|---|
| | 10 µM | 25 µM | 75 µM | 100 µM |
| NIF | 97 ± 5 | | 102 ± 5 | 108 ± 8 |
| nimodipine | 99 ± 2 | 101 ± 2 | 94 ± 4 | |
| phloretin | 110 ± 7 | 105 ± 8 | 97 ± 8 | |
| verapamil | 100 ± 2 | | 101 ± 5 | 103 ± 4 |

[a] Agents were freshly dissolved in DMSO at 10 mM and diluted into Locke just before use.
[b] PC3 cell membranes were preincubated 10 minutes with agents or control, and NT binding was performed at 22° C. for 60 minutes. Specific binding was measured in 4-6 experiments and expressed as % control (mean ± SEM). Results for the various agents were not significantly different from control ($p > 0.1$).

Example 6

Cell-surface Binding Versus Internalization

To characterize the effects of CCBs on cellular NT binding, we determined whether cell-surface binding or internalization (or both) were altered. Binding of $^{125}$I-NT to PC3 cells was performed as described in Example 1. Cell surface binding and internalization of $^{125}$I-NT were assessed by washing cells at 22° C. for 2 minutes with 0.6 ml 0.2 M acetic acid, 0.5 M NaCl, pH 3.0 (Beaudet et al., *Biochem. Pharmacol.*, 47:43-52, 1994). Binding at 4° C. achieved equilibrium within 3 hours, at which time >90% of the radioactivity was on the cell surface. Binding at 37° C. reached equilibrium in 25 minutes, at which time ≅70% of total binding was internalized. To measure rates of internalization for $^{125}$I-NT prebound to cells, the following procedure was used. $^{125}$I-NT ($10^5$ cpm) was pre-bound to PC3 cells in 24-well plates at 4° C. for 3 hours. After washing the cells three times in ice-cold PBS, >90% of $^{125}$I-NT was located on cell surface as determined by acid washing. Agents (10 mM in DMSO) were diluted to 50 µM in Locke and incubated with the cells at 37° C. for 5 minutes. The control was 0.5% DMSO. Cell-surface and internalized $^{125}$I-NT were measured, and percent internalization per minute was calculated.

Figure 4A:
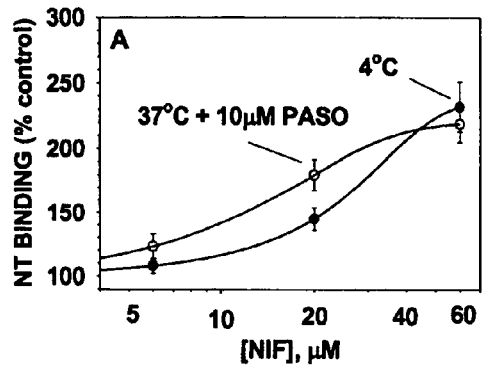
FIG. 4A is a chart showing that NIF similarly enhanced NT binding to PC3 cells at 4° C., at 37° C., and in the presence of phenylarsine oxide (PASO).
Figure 4B:
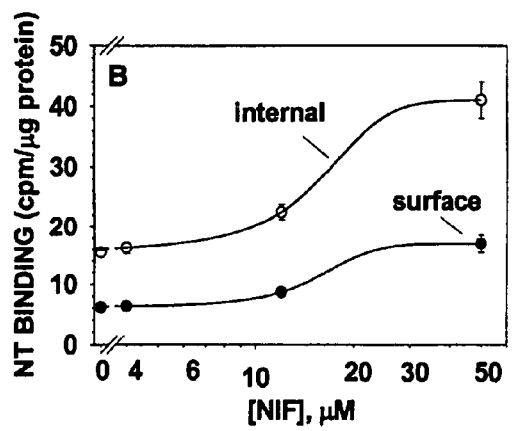
FIG. 4B is a chart showing that NIF enhanced NT binding to NTR1 (i) on the surface of the cell and (ii) internalized NTR1.

Cell-surface binding of $^{125}$I-NT was enhanced by NIF to a similar extent when assessed by three different methods (FIGS. 4A and 4B). NIF increased surface binding 2.4-, 2.2- and 2.7-fold respectively, as measured at 4° C. (FIG. 4A), at 37° C. in the presence of phenylarsine oxide (FIG. 4A), and at 37° C. by acid washing (FIG. 4B). Internalization of $^{125}$I-NT was 68-72% of total binding in the presence or absence of NIF (FIG. 4B). In addition, the internalization rate at 37° C. for cell-surface $^{125}$I-NT, previously bound to cells at 4° C. in the absence of drugs, was unaffected by 50 µM NIF, 50 µM phloretin, and 50 µM verapamil. Internalization rates (%/minute; n=12 from two experiments) were: control, 8.6±0.6; NIF, 8.0±0.6; phloretin, 8.1±0.7; verapamil, 9.2±0.7, which did not differ significantly ($p>0.1$). The results indicated that these agents increased cellular NT binding by enhancing the interaction of NT with NTR1, rather than by enhancing the internalization rate for the NT-NTR1 complex.

Example 7

Enhancement of Cellular NT-Binding by CCBs was Specific to NT

To determine whether the effects of CCBs on NT-binding to PC3 cells were receptor-specific, we measured the effects on cellular binding of ligands specific for other G-protein receptors (GPCRs) and for EGF-receptor (EGFR). Antioxidant/CCBs effects on PC3 cell binding of ligands specific for NTR, relative to other G-protein receptors GPCRs and for EGFR. Radioreceptor assays using the labeled ligands of Example 1 were developed for β2-adrenergic, bombesin and $V_{1a}$-vasopressin receptors, as well as for EGFR. Table 4 shows the ligands used and the binding parameters determined for each ligand. For NT, bombesin and EGF receptors, agonist ligands were used; for other receptors antagonists were used. Assessing the effects of CCBs, we found that NIF, phloretin, verapamil, and SKF-96365 did not enhance β2-adrenergic, $V_{1a}$-vasopressin and EGF receptor binding to PC3 cells (Table 4). However, bombesin receptor binding was elevated slightly (≅19%) by NIF (Table 4). β2-adrenergic receptor binding was actually decreased by these agents (Table 4) due to a direct competition with $^{125}$I-pindolol. This conclusion was based on the structural resemblance of these agents to pindolol and the fact that $^{125}$I-pindolol binding to PC3 cell membranes was inhibited in a similar manner (results in Table 4 footnote). Cell binding for the vasopressin receptor was also diminished by these drugs (Table 4); however, this could not be attributed to a direct competition with $^{125}$I-HOLVA (see Table 4, footnote). These data indicated that the robust elevation in ligand binding to PC3 cells caused by CCBs was specific to the NT receptor, although the bombesin receptor could also respond to a lesser degree.

TABLE 4

Effects of CCBs on PC3 Cell-binding of Ligands Specific for
Bombesin-, Vasopressin-, β2-adrenergic- and EGF-receptors

| Ligand | Agent | Specific Binding (% control) at Dose of Agent[a] | |
|---|---|---|---|
| | | 12 µM | 60 µM |
| $^{125}$I-[Nle$^{14}$]-bombesin | NIF | 108 ± 4 | 119 ± 4 ** |
| | phloretin | 104 ± 3 | 111 ± 4 |
| | verapamil | 104 ± 4 | 104 ± 4 |
| | SKF-96365 | 99 ± 2 | 106 ± 4 |
| $^{125}$I-Pindolol [b] | NIF | 105 ± 5 | 82 ± 3 ** |
| | Phloretin | 102 ± 4 | 93 ± 3 |
| | Verapamil | 68 ± 5 ** | 35 ± 6 ** |
| | SKF-96365 | 86 ± 2 ** | 51 ± 2 ** |
| $^{125}$I-HOLVA [c] | NIF | 95 ± 4 | 59 ± 5 ** |
| | Phloretin | 92 ± 4 | 73 ± 4 ** |
| | Verapamil | 85 ± 4 * | 58 ± 4 ** |
| | SKF-96365 | 80 ± 2 ** | 50 ± 2 ** |
| $^{125}$I-EGF | NIF | 100 ± 4 | 108 ± 4 |
| | Phloretin | 98 ± 2 | 95 ± 4 |
| | Verapamil | 103 ± 4 | 96 ± 4 |
| | SKF-96365 | 103 ± 3 | 94 ± 3 |

[a] Specific binding of each $^{125}$I-ligand was measured to PC3 cells. Binding was expressed as % control (mean ± SEM) for 3 to 6 independent experiments.
[b] Verapamil and SKF-96365 resemble pindolol structurally. Thus, the decrease in binding was due to direct competition with the ligand (% cross-reaction, ≅0.0005). This conclusion was supported by the fact that these agents also inhibited the binding of $^{125}$I-pindolol to PC3 cell membranes (see Methods and Table 3). Binding (% control ± SEM) for 3 experiments in duplicate was: 60 µM verapamil (9 ± 2); 60 µM SKF-96365 (18 ± 5).
[c] These agents did not resemble HOLVA structurally, and they did not inhibit the binding of $^{125}$I-HOLVA to PC3 cell membranes. Binding (% control ± SEM) for 3 experiments in duplicate was: 60 µM verapamil (91 ± 5); 60 µM SKF-96365 (110 ± 3); 60 µM NIF (90 ± 3).
* Result was significantly different from control ($p < 0.05$).
** Result was significantly different from control ($p < 0.01$).

Example 8

Inhibition of IP Formation by CCBs was Specific to NT

To examine receptor specificity, we tested the ability of NIF to inhibit IP formation in response to G protein receptor (GPCR) agonists known to stimulate PLC. IP formation was performed as described in Example 3. Preliminary dose-response experiments showed that a maximal dose of NT (30 nM), bombesin (20 nM) and ATP (10 µM) stimulated IP formation by ≅5-fold, ≅15-fold, and ≅17-fold, respectively. When PC3 cells were pretreated with varying amounts of NIF, we found that the response to this dose of NT was inhibited as much as ≅69%, whereas that for bombesin was inhibited ≅19%, and that for ATP was not inhibited (FIG. 5A). When the dose of each agonist was varied, we found that the % inhibition by 15 µM NIF was independent of the level of stimulation. Thus, at each dose, the response to NT was inhibited ≅64%, whereas that for bombesin was inhibited ≅15%, and that for ATP was not inhibited (FIG. 5B). These results indicated that the robust inhibition of IP formation by NIF was specific to NT, although the response to bombesin was also inhibited to a lesser degree.

Example 9

DHP Inhibited NT-mediated Influx of $^{45}$Ca$^{2+}$ into PC3 Cells

To determine whether CCBs altered the movement of calcium into PC3 cells, the method of Katsura et al., *Mol. Brain. Res.* 80:132-141 (2000) was used to measure $^{45}$Ca$^{2+}$ influx in response to NT. Briefly, confluent PC3 cells in 24-well dishes were washed with Ca$^{2+}$-free Locke and pretreated for 10 minutes with 0-36 µM NIF (600 µl per well). The reaction was initiated by addition of 200 µl NT, followed in 2 minutes by 2.5 mM CaCl$_2$ (5 µCi $^{45}$Ca$^{2+}$ per well). After 8 minutes, the cells were washed three times with ice-cold Locke and solubilized in 0.25 M NaOH. The cell extract was neutralized with acetic acid and scintillation counting was performed to measure $^{45}$Ca$^{2+}$ radioactivity.

Figure 6A:
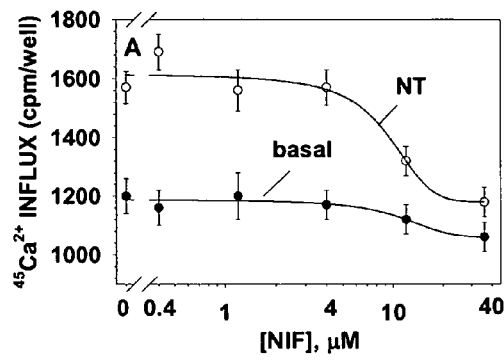
FIG. 6A is a graph showing that NIF inhibited NT-induced calcium influx, whereas NIF did not affect basal calcium influx.

NT enhanced the influx of $^{45}$Ca$^{2+}$ into PC3 cells, giving an EC50 (≅1 nM) similar to that for NT-induced IP formation. At doses shown to enhance NT binding (FIG. 1C) and to inhibit NT-induced IP formation (FIG. 2B), NIF inhibited the influx of $^{45}$Ca$^{2+}$ in response to NT (FIG. 6A). These results indicate that the effects of NIF on NT binding and IP-formation involved changes in calcium movement Example 10

Ca$^{2+}$-dependence of NT-induced IP Formation

Figure 6B:
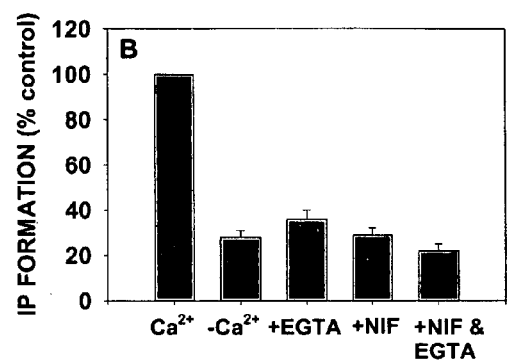
FIG. 6B is a graph showing that (i) NT-induced IP formation depends on the presence of calcium in growth media, (ii) calcium chelators prevent NT-induced IP formation, and (iii) NIF inhibits NT-induced IP formation to the same extent as calcium depletion.

Since NT caused an influx of $^{45}$Ca$^{2+}$ in PC3 cells that was inhibited by NIF, it was possible that CCBs altered NT function by blocking Ca$^{2+}$-influx. Since the enzyme that mediates IP formation (phospholipase C) was Ca$^{2+}$-dependent and since NIF blocked NT-induced IP formation and Ca$^{2+}$-influx at the same dose, we hypothesized that Ca$^{2+}$-influx was required for the IP response and that CCBs blocked this step. IP formation in response to NT was assessed as in Example 3. NT-induced IP formation was inhibited by omitting Ca$^{2+}$ from the buffer, by adding Ca$^{2+}$-chelator EGTA, or by adding NIF (FIG. 6B). Paradoxically, the removal of Ca$^{2+}$ elevated basal IP production ≅2-fold, perhaps by mobilizing internal Ca$^{2+}$-stores. However, inhibition of the NT response was not due to a ceiling effect, since IP formation could be elevated >15-fold by bombesin and ATP.

Ca$^{2+}$-ionophore (ionomycin) stimulated IP formation, reproducing ≅63% of the NT response. IP formation (% control) was: 2 µM ionomycin, 139±6% ($p<0.01$); 20 µM ionomycin, 324±14% ($p<0.01$); 30 nM NT, 457±12% ($p<0.01$). When added 2 minutes after a maximal dose of NT (30 nM), low doses of ionomycin (2-10 µM) enhanced the NT response. IP formation (% control) was: 10 µM ionomycin, 157±5 ($p<0.01$); NT, 366±20 ($p<0.01$), NT plus ionomycin, 465±9 ($p<0.001$). In contrast, a maximal dose of ionomycin gave less than additive enhancement of the NT response. IP formation (% control) was: (25 µM ionomycin, 322±11 ($p<0.001$); NT, 384±14 ($p<0.001$); NT plus ionomycin, 476±15 ($p<0.001$).

These data suggest that the inhibition of NT-induced IP formation by CCBs were at least partly attributable to a change in Ca$^{2+}$-influx.

Example 11

NT Binding to PC3 Cells was Largely Ca$^{2+}$-Independent

Figure 7:
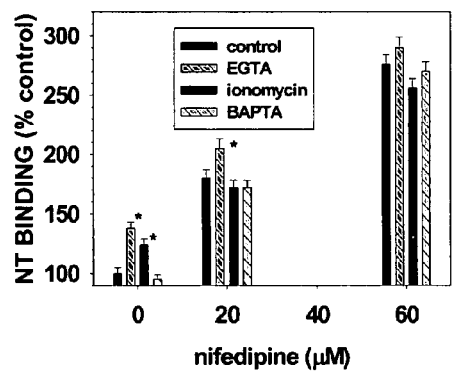
FIG. 7 is a graph showing that calcium chelators and ionophores do not affect NIF-mediated enhancement of NT binding to PC3 cells, showing that NT binding is not dependent on calcium.

To test the hypothesis that CCBs (such as NIF) altered NT binding by inhibiting Ca$^{2+}$-movement, the effects of Ca$^{2+}$-chelators and Ca$^{2+}$-ionophores on NIF-mediated enhancement of NT binding to PC3 cells were examined. Ca$^{2+}$-chelators ethylene glycol tetra-acetic acid (EGTA), and 1,2-bis (o-aminophenoxy)ethane-N,N,N',N'-tetraacetic acid tetra (acetoxymethyl) ester (BAPTA-AM) were from Sigma, and Ca$^{2+}$-ionophore ionomycin was from Calbiochem. Blocking $Ca^{2+}$-influx with 2 mM EGTA enhanced NT binding (38±6% increase; p<0.05) but the effect was small relative to the 200% increase by NIF. In addition, the ability of NIF to enhance NT binding persisted in the absence of extracellular $Ca^{2+}$. Enhancement of NT binding by NIF was not reversed by 20 µM ionomycin, nor was NT binding altered by chelation of intracellular $Ca^{2+}$ using 50 µM BAPTA-AM. Data are shown in FIG. 7.

In contrast to the results of Example 10, where the effect of NIF on NT-induced IP formation was $Ca^{2+}$-dependent, these data indicate that the effect of NIF on NT binding was $Ca^{2+}$-independent.

Example 12

$Ca^{2+}$-Channel Agonists and Antagonists Both Enhance NT Binding

Figure 8A:
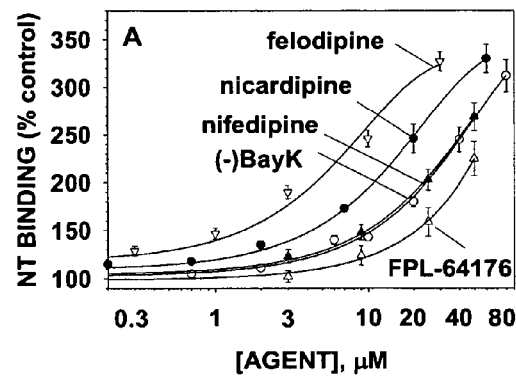
FIG. 8A is a graph showing that voltage gated calcium channel (VGCC) agonists ((−) BayK-8644, FPL-64176) and VGCC antagonists (nifedipine, nicardipine, felodipine) both enhance NT binding. Thus, enhanced NT-binding is not a function of calcium movement through these channels.
Figure 8B:
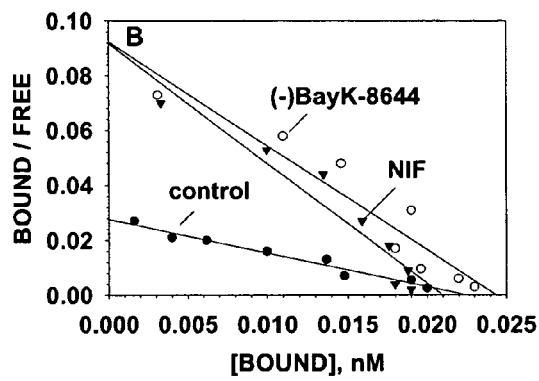
FIG. 8B is a graph showing that a VGCC agonist ((−) BayK-8644) and a VGCC antagonist (NIF) enhanced NTR1 binding affinity for NT, and did not increase NTR number.
Figure 8C:
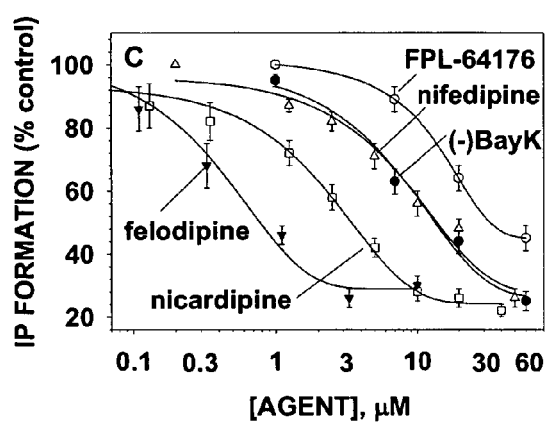
FIG. 8C is a graph showing that VGCC antagonists also enhanced NT-mediated IP formation.
Figure 8D:
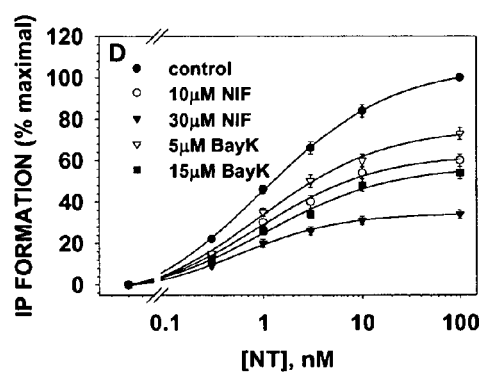
FIG. 8D is a graph showing that increased doses of VGCC antagonist (NIF) or agonist (BayK) shifted the dose response of NT-mediated IP formation downward (indicating that they affect the efficacy of NT-mediated IP formation, not the potency).

To further test the importance of $Ca^{2+}$ for the effects of CCBs on NT binding and IP formation, experiments involving $Ca^{2+}$-channel agonists and antagonists were performed using methods described in Examples 1 and 3. The results in FIG. 8A show that the VGCC agonist (−) BayK-8644 and the antagonist NIF enhanced NT binding to a similar extent. Both compounds enhanced binding by increasing NTR1 affinity, not by altering receptor number (FIG. 8B; Table 1). Another VGCC agonist FPL-64176 (Biomol, Plymouth Meeting, Pa.), known to act at a unique non-DHP site (Zheng et al., *Mol. Pharmacol.*, 40:734-41, 1991), was also active, although less potent (FIG. 8A). In addition, the agonists (−) BayK-8644 and FPL-64176 shared with the antagonist NIF an ability to inhibit NT-induced IP formation (FIG. 8C). For each agent, the NT dose-response relationship was shifted downward, indicating that the efficacy of NT was decreased, not its potency (FIG. 8D).

These results were consistent with the possible involvement of SOCC, but not VGCC, in the effects of CCBs on NTR1 function. However, this would only apply to IP formation, not to NT binding. Since IP formation was $Ca^{2+}$-dependent, the fact that these agents decreased the efficacy of NT was in keeping with their known ability to diminish SOCC conductance. However, the simplest idea was that some other property of these drugs (not involving $Ca^{2+}$) accounted for the effects of CCBs on NTR1 function.

Example 13

Agents in Combination Gave Additive Effects

Figure 9A:
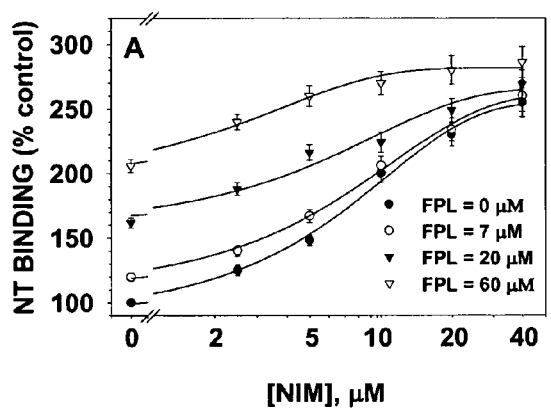
FIG. 9A is a graph showing that nimodipene (NIM) and FPL-64176 enhanced NT binding in an additive manner at low concentrations.

To further test the importance of $Ca^{2+}$-movement, dose-response studies were performed using combinations of $Ca^{2+}$-channel antagonist NIM and agonist FPL-64176, which are known to bind at distinct, discrete sites on VGCC. FIG. 9A shows that NT binding was enhanced in an additive manner at low concentrations of each drug, although the results were less than additive at high concentrations.

Figure 9B:
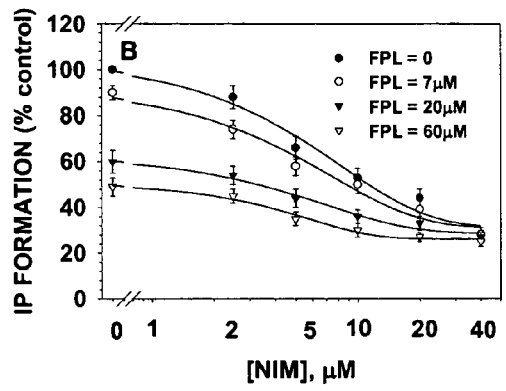
FIG. 9B is a graph showing that NT-induced IP formation was inhibited by combined doses of NIM and FPL-64176 in an additive manner at lower concentrations; inhibition of NT-mediated IP formation peaked at 70% inhibition.

FIG. 9B shows that NT-induced IP formation was inhibited in an analogous manner and at high concentrations, it reached a limit at ≅70% inhibition. Similar studies were performed using various combinations of NIF, verapamil, and diltiazem (all antagonists). Again, when low doses of these drugs were combined, additive effects were observed for the enhancement of NT binding and for the inhibition of NT-induced IP formation, whereas at high doses the effects were less than additive. No potentiative or antagonistic effects were observed.

Taken together, these results indicate that the drugs tested, whether $Ca^{2+}$-channel agonists or antagonists, acted in a similar and additive manner to alter NTR1 function.

Example 14

Effects on NTR1 Function Correlate with Antioxidant Activity

The most potent and efficacious CCBs to alter NT binding and IP formation were DHPs (such as nifedipine, nimodipine). Because DHPs are known to exhibit antioxidant ability (Mak et al., *Pharmacol. Res.*, 45:27-33, 2002), the relationship between their antioxidant activity and their ability to affect NTR1 function was investigated. DHPs were reported to inhibit $Fe^{3+}$/ascorbate stimulated lipid peroxidation in rat brain slices with activity order: nicardipine>nimodipine>nifedipine (Diaz-Araya et al., *Gen. Pharmacol.*, 31:385-91, 1998). The same activity order was found when these agents were compared for ability to (a) enhance NT binding and (b) inhibit NT-induced IP formation. In both systems, nicardipine was 2- to 4-fold more potent than nifedipine (Table 5). Felodipine was 2-to 4-fold more active than nicardipine (Table 5). While felodipine was reported to be inactive in the rat brain assay mentioned above, it was reported to be more active than nicardipine in a similar antioxidant assay using myocardial membranes (Janero and Burghardt, *Biochem. Pharmacol.*, 38:4344-4348, 1989).

The relative chemical reactivity of DHPs with superoxide anion was reported to be: felodipine>nimodipine>nifedipine>compound-1 (Ortiz et al., *Pharm. Res.*, 20:292-296, 2003). For these substances, the potency to alter NT binding correlated to antioxidant activity, giving $r^2=0.89$ (Table 5). Compound-1, a DHP analog with N-ethyl in place of the NH moiety, was reported by Ortiz et al. (supra) to have a greatly reduced reactivity with superoxide (<10% that of felodipine). Here, we found that it displayed ≅4% the activity of felodipine and 20-50% the activity of nifedipine in altering NTR function (Table 5). These results indicate that DHPs enhance NT-binding and reduce NT-mediated IP formation, by reaction(s) involving hydrogen donation, i.e., antioxidant activity.

TABLE 5

Activity of DHPs and Polyphenols on NT Binding and IP-Formation

| Classification | Agent | NT Binding [a] EC50 (µM) | IP Formation [b] IC50 (µM) | Antioxidant [c] Activity (relative) |
|---|---|---|---|---|
| VGCC antagonist | felodipine | 3 | 1 | 2.86 |
|  | nitrendipine | 7 | 2 | 1.34 |
|  | nicardipine | 7 | 3 |  |
|  | nimodipine | 7 | 6 | 2.12 |
|  | nifedipine | 15 | 15 | 0.73 |
|  | compound-1 [d] | 75 | 28 | <0.30 |
| VGCC agonist | BayK-8644 | 16 | 15 |  |
|  | FPL-64176 | 29 | 27 |  |
| Antioxidant | luteolin | 40 | 38 |  |
|  | resveratrol | 80 | 48 |  |
|  | Diphenylene iodonium | 61 | 35 |  |
|  | BHA | 110 | nd |  |

[a] EC50 was defined as the [agent] giving 75% increase in NT binding. The data are means determined in at least 3 experiments.
[b] IC50 was defined as the [agent] giving 50% decrease in IP formation. The data are means from at least 3 experiments. nd, not determined.
[c] Relative activity coefficient for reactivity to superoxide ion. Data from Ortiz et al., 2003.
[d] Compound-1 (Ortiz et al., supra, 2003) is an N-ethyl DHP (structure in FIG. 7) that displays reduced reactivity to superoxide. Its effects on calcium channels are not known.

Example 15

Effects of Other Antioxidants

ROS scavengers include vitamin-like antioxidants, flavonoids, and polyphenols (Rice-Evans et al., *Free Radic. Biol. Med.*, 20:933-956, 1996). Testing vitamin-like antioxidants (obtained from Sigma) on NT binding in PC3 cells, we found β-carotene, thiamine, riboflavin, pyridoxine, ascorbic acid, α-tocoferol, and tetrahydro-biopterin to be ineffective (used at 20-180 μM; n=3), while vitamin K (menadione) had a small effect at 180 μM (% control: 168±8; n=3; p<0.05). Other antioxidants without effect included N-acetyl cysteine, glutathione and sodium borohydride (used at 1-3 mM; n=3); trolox, ellagic acid, (+)-catechin, (−)-epigallocatechin gallate, and rutin (used at 10-100 μM; n=3).

Figure 10A:
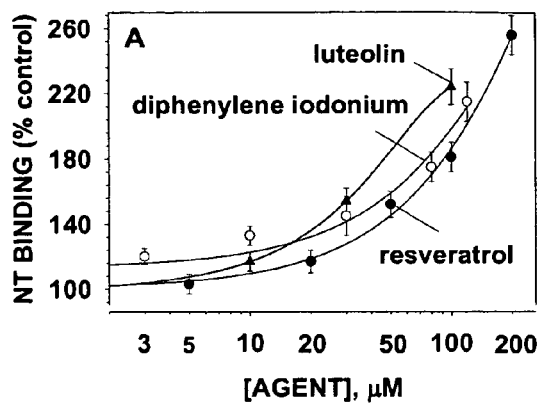
FIG. 10A is a graph showing that luteolin, resveratrol, and diphenylene iodonium (DPI) enhanced NT binding to PC3 cells.
Figure 10B:
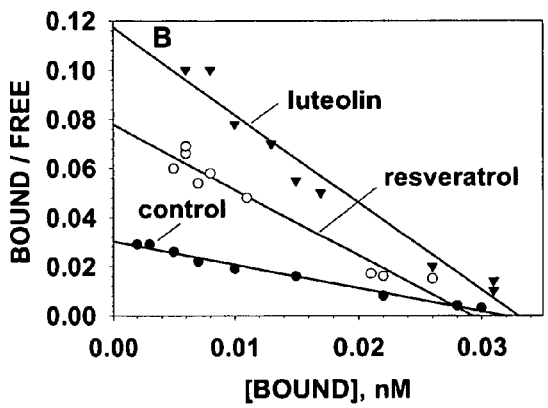
FIG. 10B is a graph showing that luteolin and resveratrol enhanced NTR affinity, not NTR number.

In striking contrast were the results for the polyphenolic antioxidants (obtained from Calbiochem), namely luteolin (a flavonoid) and resveratrol, which displayed effects that were indistinguishable from those of DHPs. Luteolin and resveratrol enhanced NT binding (FIG. 10A), and the effect involved an increase in NTR1 affinity without a significant change in NTR1 number (FIG. 10B; Table 6). Luteolin and resveratrol also inhibited NT-induced IP formation (FIG. 10C), and the effect involved a dose-dependent decrease in NT efficacy (FIG. 10D). When tested together for effects on NT binding, the response to luteolin plus nimodipine and resveratrol plus nimodipine were additive at low doses of each agent, while they were less than additive at high doses. The data demonstrate that polyphenolic antioxidants mimicked the effects of DHPs and appeared to act via the same pathway.

TABLE 6

Effects of CCBs and Antioxidants on NT Binding Parameters in PC3 Cells

| Agent[a] | Classification | Bmax[b] (fmol/mg) | Ki[b] (nM) |
|---|---|---|---|
| none | control | 155 ± 11 | 1.0 ± 0.07 |
| 50 μM nifedipine | VGCC antagonist | 152 ± 10 | 0.51 ± 0.05[c] |
| 50 μM BayK-8644 | VGCC agonist | 162 ± 12 | 0.56 ± 0.06[c] |
| 60 μM luteolin | flavonoid antioxidant | 164 ± 10 | 0.62 ± 0.05[c] |
| 150 μM resveratrol | polyphenol antioxidant | 171 ± 11 | 0.36 ± 0.04[c] |

[a] PC3 cells were pretreated 10 minutes with indicated concentrations of each agent or vehicle control. $^{125}$I-NT ($10^5$ cpm, 50 pM) was added and specific binding was measured at 37° C.
[b] Scatchard analyses were performed using 12 concentrations of NT. The results for Bmax and Ki (mean ± SEM) were from at least 3 experiments per agent.
[c] Indicates significant difference (p < 0.05) as compared to control.

Example 16

Effect of DHPs on NTR1 Does Not Involve NTR1 Sulfhydryl Groups

Since some antioxidants act by reducing sulfhydryl groups on proteins, we tested the hypothesis that DHPs increase NT binding by maintaining sulfhydryl group(s) in a reduced state. Confirming the importance of sulfhydryl groups, we showed that sulfhydryl chelators, $Ni^{3+}$ ($IC_{50}$, ≅50 μM) and $Cd^{2+}$ ($IC_{50}$, ≅600 μM), inhibited NT binding to PC3 cells, and that their effects were inhibited by 2 mM DTT.

However, in the basal state, the sulfhydryl group(s) required for NT binding to PC3 cells were primarily reduced, since NT-binding was increased only slightly by 1 mM ascorbic acid (114±7%, n=4), 2 mM DTT (125±8%, n=4) and 5 mM N-acetyl-cysteine (107±6%, n=4). 2 mM DTT did not alter the NT displacement curve and did not inhibit the effects of nifedipine. NT binding was enhanced similarly by 50 μM nifedipine in the presence and absence of 2 mM DTT (control, 246±10%; DTT, 231±11%; n=4). NT-induced IP-formation was inhibited similarly by nifedipine in the presence and absence of DTT. Thus, DHPs acted by an antioxidant mechanism that did not involve the reduction of sulfhydryl groups in NTR1.

Example 17

Effect of DHPs on NTR1 Involves Flavoprotein Dehydrogenase(s)

Diphenylene iodonium (DPI) is an inhibitor of flavoprotein dehydrogenases, enzymes that produce reactive oxygen species (ROS). To test whether DHPs scavenge ROS produced by flavoprotein dehydrogenases, the effect of DPI on NT binding to PC3 cells was tested.

Figure 10C:
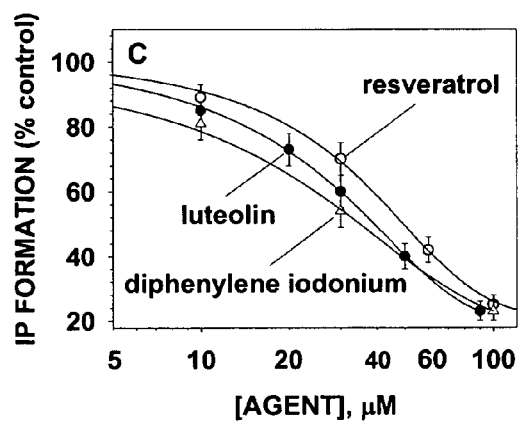
FIG. 10C is a graph showing luteolin, resveratrol, and DPI inhibited NT-mediated IP formation in PC3 cells.
Figure 10D:
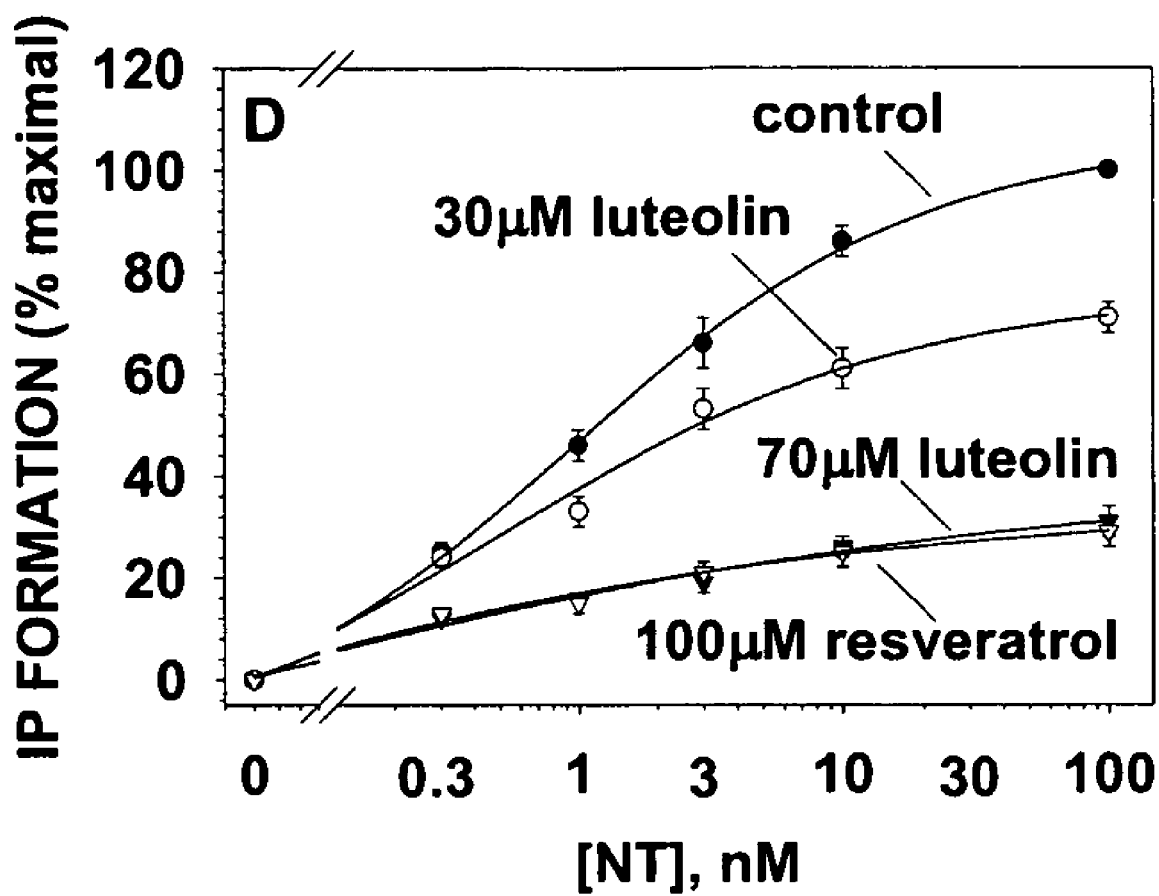
FIG. 10D is a graph showing that luteolin, resveratrol, and DPI inhibited NT-mediated IP formation in a dose-dependent decrease in NT-efficacy.

DPI mimicked the effects of DHPs on NT binding (shown in FIG. 10A) and NT-induced IP formation (shown in FIG. 10C). The hydroxy radical scavenger butylated hydroxy anisole (BHA) was also effective (Table 5). These results suggest that flavoprotein dehydrogenases and/or ROS species produced by these enzymes participate in the effects of DHPs on NTR1 function.

Example 18

Comparisons of Chemical Structures of DHPs and Polyphenols

Figure 11:
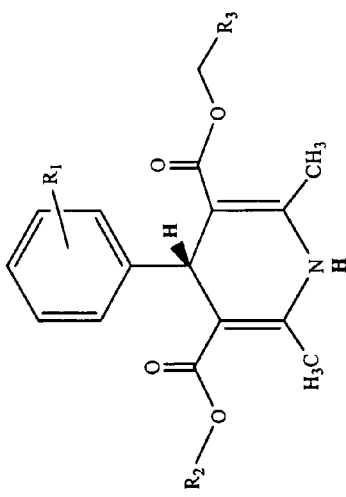
FIG. 11 is a group of chemical structures of different antioxidants.

As can be seen in FIG. 11, the chemical structures of DHPs and polyphenols are similar, each possessing aromatic ring structures with redox capability. The order of potency (Table 5) for ability to alter NTR1 function (felodipine>nitrendipine≅nicardipine>nimodipine>nifedipine>luteolin>resveratrol) appeared to relate to donor group acidity (NH>OH) and to the number of conjugated double bonds. For DHPs, chloro substituents in the adjacent phenyl ring gave the highest activity (felodipine), while nitro in the meta position was less effective (nitrendipine, nicardipine, nimodipine) and nitro in the ortho position was least effective (nifedipine). Luteolin and resveratrol contained conjugated π-bonded rings which could potentially support the stability of radicals and cations (Solomons, Chapter 15, in Fundamentals of Organic Chemistry, pp. 599-641, 4th ed., John Wiley & Sons, NY 1994). By donating hydrogen(s), DHPs could conceivably form pyridinium or pyridine analogs with an even greater number of conjugated double bonds and potential to support radical and cation formation. The very high membrane partition coefficients displayed by DHPs (Mason et al., *Biophys. J.*, 56:1193-201, 1989) could determine their ability to accumulate at target site(s).

Figure 12A:
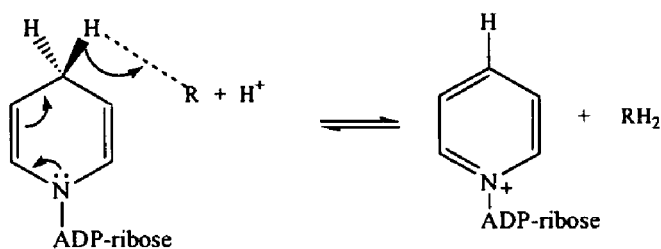
FIG. 12A is a reaction scheme for hydrogen donation by NADH.
Figure 12B:
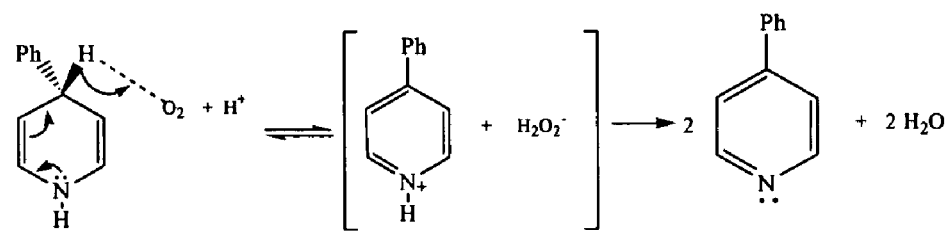
FIG. 12B is a possible reaction scheme for hydrogen donation by DHPs.
Figure 12C:
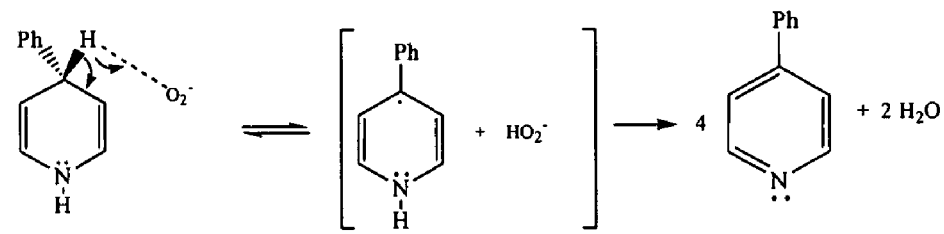
FIG. 12C is another possible reaction scheme for hydrogen donation by DHPs.

The reaction scheme whereby NAD-linked dehydrogenases donate hydrogen atoms to substrates is shown in FIG. 12A. One hydrogen is transferred from NADH as a hydride ion ($H^-$) and another is taken as $H^+$ from the medium (Lehninger, Chapter 17, in *Principles of Biochemistry, pp. 477*, Anderson et al., eds), Worth Publishers, New York, 1982). While not intending to be bound by theory, it is possible that DHPs can react analogously, transferring hydrogen atoms to superoxide by way of cationic (FIG. 12B) or radical intermediates (FIG. 12C) to generate pyridine derivatives and water. DHPs are known to form pyridine adducts when reacted with alkyl radicals (Nunez-Vergara et al., *Free Rad. Res.*, 37:109-

120, 2003). Since the stability of the intermediates in FIGS. 16A-16C is negatively affected by electron withdrawal, this predicts that nitro groups in the phenyl ring (especially ortho) would diminish reactivity. The order derived from such considerations (felodipine>nitrendipine≅nicardipine≅nimodipine>nifedipine) is in fair agreement with that measured by Ortiz et al., *Pharm. Res.*, 20:292-296, 2003, and that found here for altering NTR1 function. Since nitrendipine, nicardipine, and nimodipine each have nitro in the meta position, a near equal reactivity with superoxide is expected. The differences in their activity in our system might be attributed to the effects of other ring substituents on lipophilicity (FIG. 11), which could affect their ability to enter cells and partition into membranes.

Example 19

Lipoxygenase (LOX) Expression in PC3 Cells

Figure 13:
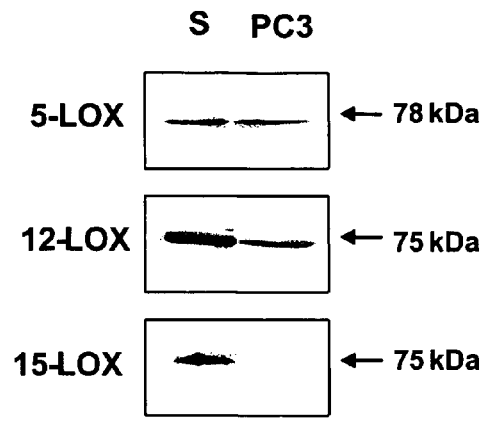
FIG. 13 is an image of an immunoblot showing that PC3 cells expressed 5-lipoxygenase (5-LOX) and 12-lipoxygenase (12-LOX).

To investigate whether other oxidative systems could potentially contribute to the enhancement of NT binding by antioxidants, we assessed the expression of lipoxygenases (LOXs) in PC3 cells. LOXs are lipid-peroxidizing enzymes categorized according to specificity for oxygenation of arachidonic acid; they include 5-LOX, 12-LOX and 15-LOX. Metabolism of arachidonic acid via the LOX pathway has been reported to generate ROS. See, e.g., Nakamura et al., *Carcinogenesis*, 6:229-235, 1985. To determine which LOX isoforms might be involved in the regulation of NT binding and signaling, we examined PC3 cell extracts for the presence of these proteins. Western blotting was performed using specific antisera to 5-LOX, 12-LOX and 15-LOX (Cayman Chemical, Ann Arbor, Mich.). LOX isoforms have predicted molecular weights in the range 75-80 kDa (Brash et al., *J. Biol. Chem.*, 274:23679-82, 1999). As shown in FIG. 13, PC3 cell extracts tested positively for 5-LOX and 12-LOX, giving bands corresponding to the standard. On the other hand, 15-LOX appeared not to be present in PC3 cells. These findings indicate the presence of proteins similar to 5-LOX and 12-LOX in PC3 cells that could be the targets of LOX inhibitor class of antioxidants.

Example 20

Antioxidants that are LOX Pathway Blockers Enhanced NT Binding

In the following experiments, the antioxidants MK886, LY171883, LY294002, and SB203580 were from Calbiochem (San Diego, Calif.). The antioxidants Rev-5901, AA861, retinoic acid, LY83583, and SQ22536 were from Biomol (Plymouth Meeting, Pa.). The antioxidants Nordihydroguaiaretic acid (NDGA), caffeic acid phenethyl ester (CAPE), gossypol, and 5,8,11,14-eicosatetraynoic acid (ETYA) were from Sigma (St. Louis, Mo.).

Figure 14A:
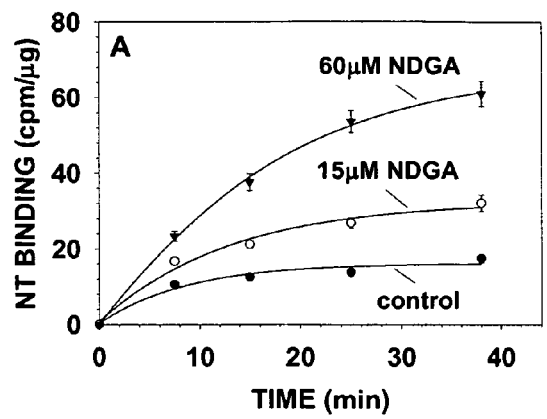
FIG. 14A is a graph showing that nordihydroguaiaretic acid (NDGA) enhanced NT binding to PC3 cells.
Figure 14B:
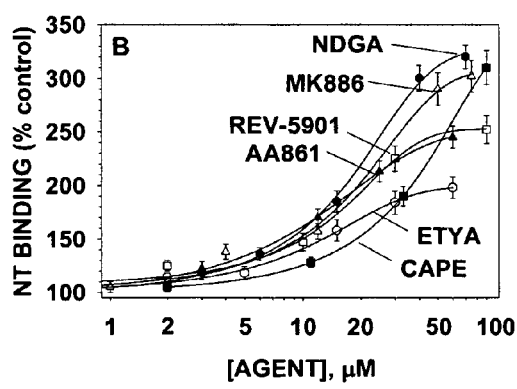
FIG. 14B is a graph showing that a number of nonselective lipoxygenase (LOX) inhibitors enhanced NT binding to PC3 cells.
Figure 14C:
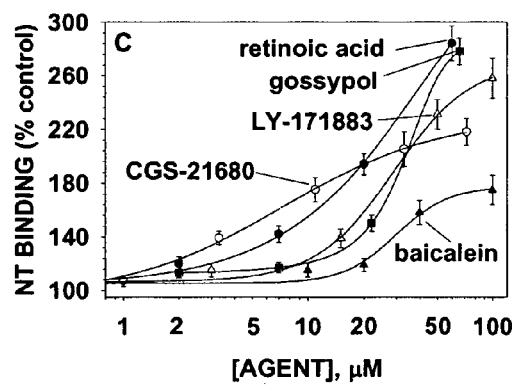
FIG. 14C is a graph showing that other nonselective LOX inhibitors also enhanced NT binding to PC3 cells.

Specific binding of $^{125}$I-NT ($10^5$ cpm/ml) to PC3 cells at 37° C. (≅95% of total binding) was ≅16.8±0.81 cpm $^{125}$I-NT bound/μg protein (n=12), which corresponded to ≅3000 cpm $^{125}$I-NT bound/well. NDGA, a broad specificity LOX inhibitor, dose-dependently increased the apparent rate of and the steady state level of NT binding to PC3 cells (FIG. 14A). Specific binding was enhanced as much as 3-fold, without a change in non-specific binding.

Similar effects were displayed by eleven structurally diverse LOX pathway blockers that acted by a number of different mechanisms. These included four non-selective LOX inhibitors (NDGA, ETYA, CAPE, gossypol), two 5-LOX inhibitors (AA-861, Rev-5901), one FLAP inhibitor (MK886), two inhibitors of leukotriene formation (retinoic acid, CGS-21680), one LTD4 receptor antagonist (LY171883) and one 12-LOX inhibitor (baicalein). NT binding was increased dose-dependently up to 3.2-fold by NDGA, 3.0-fold by MK886, 2.8-fold by CAPE, 2.7-fold by retinoic acid, 2.6-fold by LY-171883, 2.6-fold by gossypol, 2.4-fold by Rev-5901, 2.3-fold by AA-861, 2.2-fold by ETYA, 2.2-fold by CGS-21680 and 1.8-fold by baicalein (FIGS. 16B and 16C). The specificity of these drugs and the magnitude of their effects on NT binding suggested that the primary target was likely to be 5-LOX, rather than 12-LOX or 15-LOX.

Example 21

LOX Pathway Blockers Inhibit NT-induced IP Formation

Although antioxidants that are LOX-inhibitors enhanced NT receptor binding, they reduced the ability of NT to stimulate phospholipase C. NT increased IP formation in PC3 cells with an EC50 value of ≅1 nM (FIG. 15A), which was in agreement with the receptor Kd (Carraway et al., *J. Pharmacol. Exp. Ther.*, 307:640-50, 2003). LOX pathway blockers dose-responsively inhibited NT-induced IP formation (e.g., FIG. 15B). The efficacy of NT was reduced, not its potency (FIG. 15A), suggesting that these agents either shifted NTR1 to a non-functional state or they decreased the reaction rate by inhibiting phospholipase C or diminishing substrate levels.

For each of the agents examined (Table 7), the IC50 value for inhibiting NT-induced IP formation was related to the EC50 value for enhancing NT binding, and there was a strong statistical correlation ($r^2$=0.94). The data thus indicate that these two responses had a similar chemical sensitivity to the (antioxidant) LOX inhibitor drugs tested and/or that they were linked, e.g., that one led to the other.

TABLE 7

Activity of LOX Blockers on NT Binding and NT-induced IP Formation

| Inhibitor Type | Agent | NT Binding [a] | | IP Formation [b] | 5-LOX Activity [c] |
|---|---|---|---|---|---|
| | | Efficacy % increase | EC50 μM | IC50 μM | IC50 μM |
| non-selective LOX inhibitors | NDGA | 230 | 16 | 7 | 0.3-2 |
| | ETYA | 100 | 50 | 32 | 6-50 |
| | CAPE | 220 | 34 | 18 | |
| | Gossypol | 170 | 32 | 20 | |
| 5-LOX Inhibitors | Rev5901 | 160 | 19 | 8 | 10 |
| | AA861 | 155 | 19 | 7 | 0.1-2 |

TABLE 7-continued

Activity of LOX Blockers on NT Binding and NT-induced IP Formation

| | | NT Binding [a] | | IP Formation [b] | 5-LOX Activity [c] |
|---|---|---|---|---|---|
| Inhibitor Type | Agent | Efficacy % increase | EC50 μM | IC50 μM | IC50 μM |
| FLAP Inhibitor | MK886 | 210 | 18 | 8 | 0.1-1 |
| 12-LOX Inhibitor | Baicalein | 75 | >100 | >100 | |
| Blockers of Leukotriene Formation | Retinoic Acid | 180 | 20 | 7 | |
| | CGS21683 | 228 | 22 | nd | 0.01-1 |
| LTD4 receptor Antagonist | LY171883 | 157 | 34 | nd | |

[a] EC50 was defined as the [agent] giving 100% increase in NT binding. Data are means from at least 3 experiments.
[b] Since the maximal inhibition of IP formation was ≅80%, IC50 was defined as [agent] that decreased IP formation by 40%. Data are means determined in at least 3 experiments.
[c] IC50 is given as the range of reported values for inhibition of 5-LOX activity measured in various blood cell systems (Walker et al., 2002; Flamand et al., 2000; Ford-Hutchinson et al., 1994; Radmark, 2000; and references therein).

Example 22

LOX Pathway Blockers Do Not Act Directly on NTR1

Binding of $^{125}$I-NT to isolated PC3 cell membranes in vitro was not dramatically increased by NDGA, MK886, Rev-5901, AA-861 and retinoic acid (Table 8), suggesting that LOX-directed agents did not act directly on isolated NTR1. Although a key participant in the reaction might have been lost during membrane isolation, it seems more likely that there was a requirement for cellular metabolism and/or architecture. Thus, the increase in NT binding observed in live cells most likely reflected an indirect effect possibly involving inhibition of ROS production by the LOX pathway (See FIG. 20).

TABLE 8

Effects of LOX Pathway Blockers on NT-binding to PC3 Cell Membranes

| | Specific NT-Binding (% control) at Dose of Agent [a] | | |
|---|---|---|---|
| Agent | 10 μM | 25 μM | 75 μM |
| NDGA | 110 ± 5 | 121 ± 8 | 132 ± 10 * |
| MK886 | 99 ± 3 | 107 ± 4 | 97 ± 4 |
| Rev-5901 | 101 ± 4 | 113 ± 5 | 110 ± 5 |
| AA-861 | 107 ± 4 | 109 ± 4 | 110 ± 5 |
| Retinoic acid | 102 ± 3 | 115 ± 4 * | 142 ± 8 ** |

[a] PC3 cell membranes were preincubated for 10 minutes with agents or control, and NT binding was performed at 22° C. for 60 minutes. Specific binding was measured in four experiments and expressed as % control (mean ± SEM).
* Result was significantly different from control (p < 0.05).
** Result was significantly different from control (p < 0.01).

Example 23

Receptor Specificity

To determine if the effects were specific to NTR1, we tested LOX pathway blockers for effects on PC3 cell binding of ligands for other receptors using assays previously described above. The results in Table 9 show that that NDGA, MK886, AA861, and Rev-5801 did not have dramatic effects on the binding of ligands for the bombesin, $V_{1a}$-vasopressin, β2-adrenergic and EGF receptors. There was only a modest increase (19-35%) in bombesin receptor binding (all agents) and a 65% increase in EGF binding (only MK-886). The 24-34% decrease in β2-adrenergic receptor binding was likely due to structural similarity of the agents to epinephrine. Thus, the robust elevation in cell binding (>200% increase) caused by LOX-directed agents was specific to NTR1.

TABLE 9

Effects of LOX Blockers on PC3 Cell Binding of Ligands Specific for Bombesin-, Vasopressin-, β2-adrenergic- and EGF-receptors

| | | Specific Binding (% control) at Dose of Agent [e] | |
|---|---|---|---|
| Ligand | Agent | 12 μM | 60 μM |
| $^{125}$I-[Nle14]-bombesin [a] | NDGA | 110 ± 3 | 127 ± 4 ** |
| | MK886 | 106 ± 5 | 125 ± 7 * |
| | AA-861 | 112 ± 4 | 135 ± 6 ** |
| | Rev-5901 | 107 ± 3 | 119 ± 3 ** |
| $^{125}$I-HOLVA [b] | NDGA | 84 ± 4 ** | 50 ± 4 ** |
| | MK886 | 93 ± 5 | 67 ± 3 ** |
| | AA-861 | 87 ± 3 * | 57 ± 3 ** |
| | Rev-5901 | 68 ± 5 ** | 42 ± 3 ** |
| $^{125}$I-Pindolol [c] | NDGA | 86 ± 4 * | 66 ± 9 ** |
| | MK886 | 105 ± 3 | 102 ± 6 |
| | AA-861 | 107 ± 5 | 102 ± 6 |
| | Rev-5901 | 97 ± 2 | 76 ± 3 ** |
| $^{125}$I-EGF [d] | NDGA | 114 ± 4 | 112 ± 6 |
| | MK886 | 141 ± 7 ** | 165 ± 11 ** |
| | AA-861 | 112 ± 5 | 100 ± 3 |
| | Rev-5901 | 101 ± 3 | 92 ± 5 |

[a] This ligand for bombesin receptor gave 95% specific binding (Bmax = 1016 ± 64 fmol/mg).
[b] This ligand for $V_{1a}$-vasopressin receptor gave 77% specific binding (Bmax = 156 ± 12 fmol/mg). None of the agents resembled HOLVA structurally.
[c] This ligand for β2-adrenergic receptor gave 66% specific binding (Bmax = 86 ± 6 fmol/mg). Since NDGA and Rev-5901 resemble epinephrine structurally, the decrease in binding was most likely due to direct competition with the ligand (% crossreaction, ≅0.0005).
[d] This ligand for EGF-receptor gave 95% specific binding (Bmax = 151 ± 11 fmol/mg).
[e] Specific binding of each $^{125}$I-ligand was measured to PC3 cells at 37° C. Binding was expressed as % control (mean ± SEM) for at least three independent experiments.
* Result was significantly different from control (p < 0.05).
** Result was significantly different from control (p < 0.01).

Example 24

Specificity for LOX Pathway

NT binding was not dramatically altered by inhibitors of cyclooxygenase (indomethacin, phenbutazone), nitric oxide synthase (L-NAME, L-NMMA), guanylyl cyclase (LY83583), adenylyl cyclase (SQ22536), and various protein kinases (PD98059, LY294002) at concentrations known to affect these enzymes (Table 10). NT binding was also not much affected by general reducing agents (e.g., sodium borohydride, dithiothreitol) and antioxidants (e.g., trolox, ascorbic acid, thianin, riboflavin, pyridoxine). Inhibitors, chemicals, and antioxidants tested were from Sigma. Thus, it was unlikely that the robust effects of LOX inhibitors involved non-specific actions or general effects on protein sulfhydryl groups.

These results indicated that the robust effects of LOX inhibitors were not likely to involve non-specific actions or general effects on protein sulfhydryl groups.

(n=8). The surface-bound $^{125}$I-NT and the internalized $^{125}$I-NT were both dose-dependently enhanced by NDGA (FIG. 16A) and MK886 (FIG. 16B). Internalization, as percentage of total binding, was unchanged by these agents (range for all groups: 68-73%). NDGA and MK886 also enhanced $^{125}$I-NT binding similarly under conditions where internalization was fully inhibited by 10 µM phenylarsine oxide (results not shown). In addition, the rate of internalization at 37° C. for cell-surface $^{125}$I-NT, previously bound to cells at 4° C., was unaffected by 50 µM NDGA [uptake rate (%/min): control, 9.5±0.8; NDGA, 10.2±0.9; n=8]. These results indicated that LOX pathway blockers increased cellular NT binding by enhancing the interaction of NT with NTR1, rather than by enhancing internalization of the NT-NTR1 complex.

These results indicate that LOX pathway blockers increased cellular NT binding by enhancing the interaction of

TABLE 10

Effects of Various Enzyme Inhibitors on NT Binding to PC3 Cells

| Agent[a] | Enzyme | Specific NT-Binding (% control) at Dose of Agent[b] | | | |
|---|---|---|---|---|---|
| | | 6 µM | 20 µM | 60 µM | 200 µM |
| indomethacin | cyclooxygenase | 109 ± 4 | 95 ± 6 | 113 ± 7 | |
| phenylbutazone | cyclooxygenase | 113 ± 4 | 100 ± 4 | 89 ± 9 | |
| L-NAME | NO synthase | 101 ± 3 | 103 ± 4 | 95 ± 6 | |
| L-NMMA | NO synthase | 103 ± 5 | 107 ± 3 | 105 ± 7 | |
| LY83583 | guanylyl cyclase | 106 ± 4 | 96 ± 5 | 95 ± 6 | |
| SQ22536 | adenylyl cyclase | 98 ± 3 | 108 ± 4 | 105 ± 4 | |
| PD98059 | MAPK-kinase | 113 ± 7 | 121 ± 7 * | 131 ± 9 * | |
| U0126 | MAPK-kinase | 118 ± 6 | 108 ± 6 | 120 ± 9 | |
| LY294002 | PI3-kinse | 115 ± 9 | 118 ± 6 * | 132 ± 8 | |
| SB203580 | p38 MAP kinase | 108 ± 8 | 116 ± 7 | 125 ± 9 | |

[a] L-NAME and L-NMMA were dissolved in water and all other agents were in DMSO at 10 mM. Agents were diluted into Locke just before use.
[b] PC3 cells were preincubated with agent or control vehicle for 10 minutes prior to the NT binding reaction. Specific NT binding is given as % control (mean ± SEM) for at least three independent experiments.
* Results were significantly different from control (p < 0.05).

Example 25

LOX Pathway Blockers Enhance Photoaffinity Labeling of NTR1

NTR1 has been labeled using UV-activatable cross linkers (Mazella et al., *J. Biol. Chem.*, 263:144, 1988). Antiserum to NTR1 was used to immunoprcipitate NTR1 after UV-crosslinking of PC3 cells with $^{125}$I-(4-azido-Phe$^6$)-NT in the presence and absence of LOX pathway blockers using methods described in Example 4. Radioactivity associated with NTR1 was enhanced 2.6±0.3-fold and 2.7±0.3-fold by 50 µM NDGA and MK886, respectively. For each agent, the increase in immunoprecipitated radioactivity was similar to the increase in NT binding to PC3 cells at the dose used (FIG. 15B). These results indicate that LOX pathway blockers enhance NT binding by increasing the association of $^{125}$I-NT with NTR1; however, they do not rule out possible interactions with other NT receptors.

Example 26

Cell-surface Binding Versus Internalization

Acid washing of PC3 cells after binding of $^{125}$I-NT to the cells indicated that 72±2% of the $^{125}$I-NT was internalized NT with NTR1. As was expected, these drugs also increased the total amount of NT-NTR complex internalized by the cell; however, they did not alter the rate of internalization or the percentage of bound NT that was internalized.

Example 27

NTR1 Affinity Versus NTR1 Number

LOX pathway blockers enhanced binding and increased the steepness of the NT displacement curve. When NT displacement data were expressed as % maximal binding, LOX pathway blockers shifted the displacement curves to the left by a factor of ≅3 (FIG. 18A). In three experiments, the average Ki for NT was decreased from 1.0±0.09 nm (control) to 0.28±0.05 nm (50 µM NDGA; p<0.01) and 0.35±0.05 nm (50 µM MK886; p<0.01). Scatchard analyses indicated that NDGA and MK886 increased the affinity of NTR1 for NT without changing receptor number (FIG. 17B; Table 5).

Taken together, these results indicated that LOX pathway blockers shifted NTR1 towards a state that displayed an increased affinity for the agonist NT.

TABLE 11

Effects of LOX Pathway Blockers on NT Binding Parameters

| Agent[a] | Bmax[b] (fmol/mg) | Ki for NT[b] (nM) |
|---|---|---|
| control | 145 ± 9 | 1.0 ± 0.09 |
| NDGA | 128 ± 10 | 0.28 ± 0.03 ** |
| MK886 | 143 ± 12 | 0.35 ± 0.04 ** |

[a] PC3 cells were pretreated 10 minutes with 50 μM concentrations of each agent or vehicle control. $^{125}$I-NT ($10^5$ cpm, 50 pM) was added and specific binding was measured at 37° C.
[b] Scatchard analyses were performed using 12 concentrations of NT and results for Bmax and Ki (mean ± SEM) were from at least three experiments for each agent.
** Result is significantly different from control ($p < 0.01$).

Example 28

PKC-Inhibitors Enhance NT Binding and Inhibit IP Formation

Protein kinase C is a family of enzymes that play key roles in tumor promotion and progression (Gopalakrishna, et al., *Free Rad. Biol. Med.*, 28:1349-1361, 2000). Activation of PKC can stimulate cellular production of reactive oxygen species (ROS) (Inoguchi et al., *J. Am. Soc. Nephrol.*, 14:S227-S232, 2003). Antioxidants can inactivate PKC and this may be responsible for the inhibitory effects of antioxidants on cancer cell growth and tumor promotion (Gopalakrishna et al., *J. Nutr.*, 132:3819 S-3823S, 2002). These findings led us to investigate the effects of PKC inhibitors on NT binding and IP formation.

For IP assays, PC3 cells were treated 10 minutes with PKC inhibitors (from Sigma), then stimulated 30 minutes with NT before IP levels were evaluated using methods in Example 3. For binding assays, PC3 cells were treated 10 minutes with agents, and NT receptor binding was evaluated at 37° C. using methods described in Examples 1 and 2.

Figure 19A:
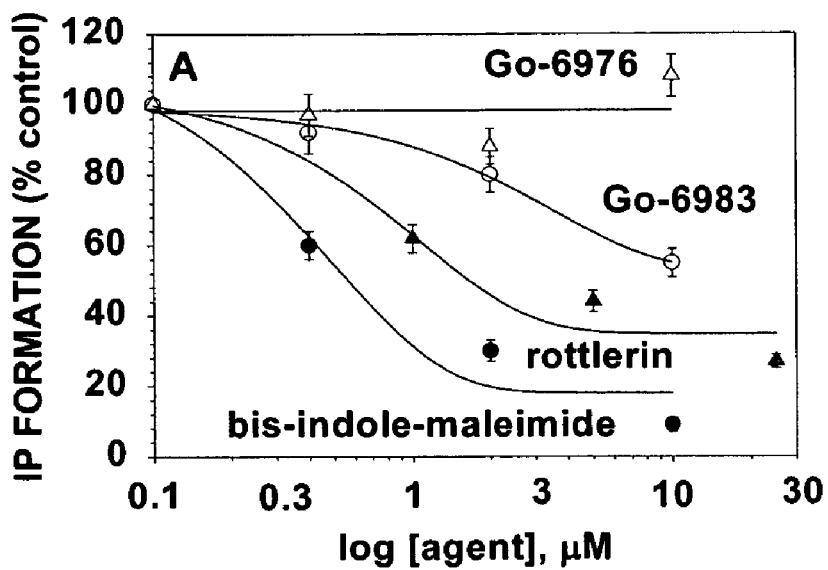
FIG. 19A is a graph showing the effects of several protein kinase C (PKC) inhibitors on NT binding to PC3 cells.
Figure 19B:
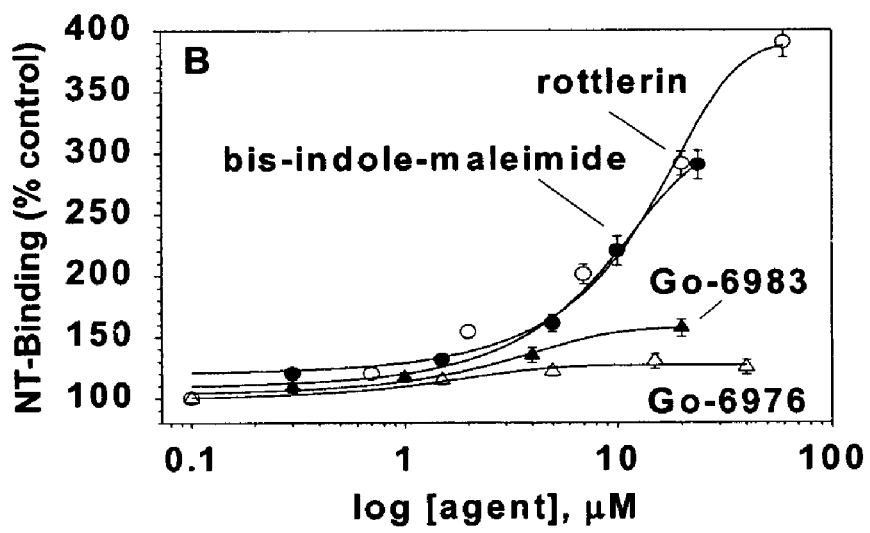
FIG. 19B is a graph showing the effects of several PKC inhibitors on NT-mediated IP formation in PC3 cells.

Inhibitors of novel PKCs inhibited NT-induced IP formation (FIG. 19A) and enhanced NT binding up to 4-fold. (FIG. 19B). The order of efficacy in the two assays correlated (BIS≅rottlerin>Go6983>>Go6976), indicating involvement of novel PKCs ($\delta, \epsilon, \eta, \theta$) but not conventional PKCs ($\alpha$, $\beta 1$, $\beta 2$, $\gamma$) in the effects.

The results demonstrate that inhibitors of novel PKCs mimic the effects of CCBs, DHPs, LOX inhibitors, polyphenols and other antioxidants.

Example 29

Inhibitors of Mitochondrial Function Enhance NT Binding

The mitochondrial electron transport chain is the most notable source of ROS in most cells (McLennan et al., *J. Bioenerg. Biomemb.*, 32:153-162, 2000). To further examine the link between ROS formation and NTR function, we used inhibitors of mitochondrial function to reduce cellular ROS and tested the effects on NT binding and IP formation. The methods used were similar to those described in Example 28. Carbonyl cyamide 3-chlorophenylhydrozone (CCCP), antimycin A, myxothiazol, and rotenone were obtained from Sigma, dissolved at 10 mM in DMSO, and diluted just before use.

Rotenone (inhibitor of complex I), antimycin A, and myxothiazol (inhibitors of complex III), and CCCP($H^+$ ionophore) all of which would be expected to alter ROS production, elevated NT binding by as much as 3-fold. The EC50 for the increase in NT binding was: rotenone (38 μM), antimycin A (32 μM), myxothiazol (16 μM), and CCCP (23 μM). These results indicate that inhibitors of mitochondrial ROS production are similar to antioxidants in that they enhance cellular NT binding.

Example 30

Effects of Antioxidant Agents in NT Assays Reflect Anticancer Activity

We have shown that a variety of antioxidant drugs elevate NT binding and inhibit IP formation in cancer cells. Since many antioxidant drugs are anticancerous, we propose to use the NT assays as indicators of the anticancer activity for such drugs. To test this idea, we performed parallel assays for a number of antioxidants and compared the results.

Anticancer activity was assessed using methods from Hassan et al., *Regul. Pept.*, 120:155-166 (2004) and these are described here in brief form. Western blotting was used to assess activation of growth pathways. In particular we measured the activation of a MAP-kinase called ERK using antibodies specific for the phosphorylated form. Serum was withdrawn for 24 hours from 80% confluent PC3 cells in 60 mm dishes. Cells were washed in Locke, then exposed for 3 minutes to 10 nM NT as stimulus. Reactions were stopped on ice, and cells were washed in buffer containing phosphatase and protease inhibitors. Cells were extracted into 2×SDS buffer, and proteins were separated by SDS-PAGE using 10% mini-gels. Proteins were electroeluted onto PVDF, and blots were blocked in non-fat dry milk in TTBS buffer. Blots were incubated with the primary antibody in blocking buffer for 18 hours at 4° C., washed in TTBS, then incubated with horseradish peroxidase-linked secondary antibody for 1 hour at 20° C. Enhanced chemoluminescence was performed according to manufacturer (Santa Cruz) and autoradiographs were scanned for computerized densitometric analysis. The results for the phospho-ERK were normalized by stripping the blots and reprobing with antibodies that measured the total ERK concentration.

To assess cell proliferation, $10^4$ cells were plated in 24-well plates and, after 24 hours, cells were serum-starved for 48 hours, and fresh medium was added with the test compounds. After 30 minutes, 10 nM NT was added as stimulus. After 24 hours, the cells were pulsed with $^3$H-thymidine, DNA was precipitated with 6% TCA, washed in PBS and ethanol, then solubilized in NaOH-SDS and subjected to liquid scintillation counting.

Figure 21A:
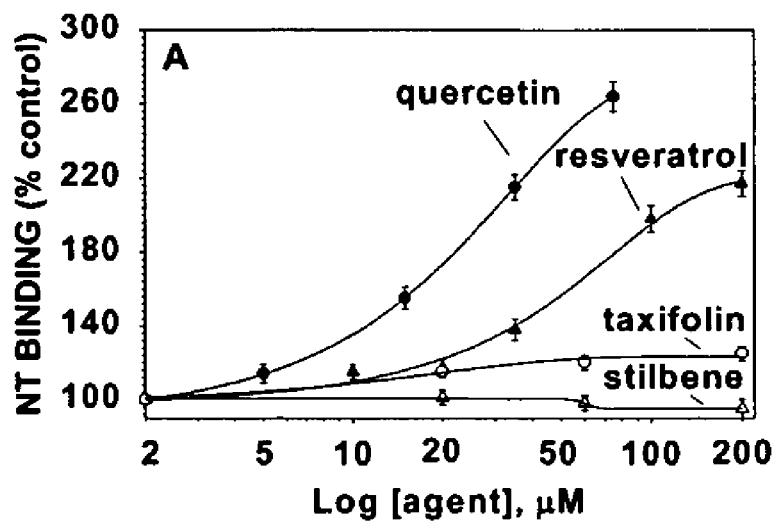
FIG. 21A is a graph showing that quercetin and resveratrol enhanced NT-binding to NTR at similar concentrations as were required for these compounds to demonstrate mitogen activating protein kinase inhibitory activity.
Figure 21B:
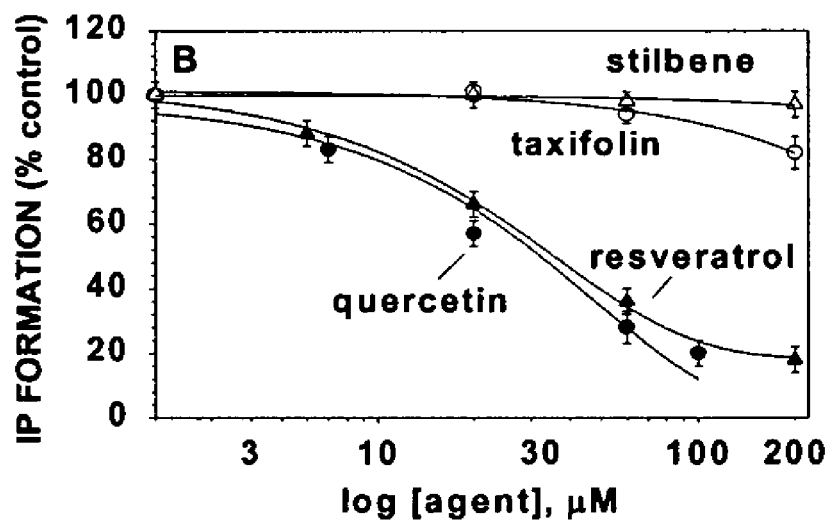
FIG. 21B is a graph showing that quercetin and resveratrol inhibited NT-induced IP formation at similar concentrations as were required for these compounds to demonstrate mitogen activating protein kinase inhibitory activity.

In testing flavonoids and polyphenols, we found that quercetin and resveratrol inhibited NT-induced ERK activation and cell proliferation, whereas the closely related chemical structures taxifolin and stilbene were inactive. The IC50s for the effects of quercetin (25 μM) and resveratrol (50 μM) on ERK activation agreed with the IC50s for the effects on NT-binding and IP formation (FIGS. 21A and 21B, respectively). In order to measure cell proliferation, the cells were exposed to the drugs for much longer times (24 hours versus 3 minutes) and as a result, the IC50s were lower (0.5 μM and 3 μM). The finding that quercetin and resveratrol (but not taxifolin and stilbene) are antiproliferative is in general agreement with the literature (O'Prey et al., *Biochem. Pharmacol.*, 66:2075-2088, 2003; Mouria et al., *Int. J. Cancer*, 98:761-769, 2002; Casagrande et al., *Biochem. Pharmacol.*, 61:1205-1215, 2001; and references therein).

In testing 1,4-dihydropyridines (DHPs), we found that a series of agents displayed an efficacy order for inhibiting NT-induced proliferation of PC3 cells (nicardipine>nifedipine>compound I) that was identical to that for the effects on NT binding and IP formation (see results in Example 14). The IC50's for inhibition of proliferation were: nicardipine (0.1 µM), nifedipine (4 µM) and compound I (>10 µM).

These results indicate that the NT assays accurately assess the antiproliferative activity for a series of polyphenolic antioxidants and DHP-type antioxidants. In contrast, chemical assays for the antioxidant activity of these compounds (Rice-Evans et al., *Free Rad. Biol. Med.*, 20:933-956, 1996; and references therein), as well as biological assays performed in vitro (Ozgova et al., *Biochem. Pharmacol.*, 66:1127-1137, 2003; Mitchell et al., *Arch. Biochem. Biophys.*, 360:142-148, 1998; and references therein) do not give results that correlate to anticancer behavior (O'Prey et al., *Biochem. Pharmacol.*, 66:2075-2088, 2003; Mouria et al., *Int. J. Cancer*, 98:761-769, 2002; Knowles et al., *Nutr. Cancer*, 38:116-122, 2000; Casagrande et al., *Biochem. Pharmacol.*, 61:1205-1215, 2001; Huang et al., *Br. J. Pharmacol.*, 128:999-1010, 1999; and references therein).

These results indicate that NT assays are unique in selectively responding to specific subsets of antioxidants that act directly or indirectly to target mechanisms operating within cancer cells that are associated with antiproliferative activity.

Example 31

Agents Identified in Anticancer Literature React in NT Assays

To assess the utility of the NT binding assay for the detection of drugs with anticancer activity, various compounds that were known of have anticancer actions identified in the literature were tested for the ability to enhance NT binding in PC3 cells. Each agent, dissolved in DMSO at 10 mM, was diluted into Locke and tested in the NT binding assay as described in Examples 1 and 2. All of the compounds listed in Table 12 were anticancerous and each of them was found to elevate NT binding. Although these various compounds are thought to target different mechanisms to induce their anticancer effects, the fact that they all elevated NT binding suggests that their actions had an associated antioxidative effect. These results indicate that the NT assays could provide a useful means to search for agents possessing anticancer activity.

TABLE 12

Detection of Anticancer Agents Using NT Binding Assay

| Proposed Target | Agent | Anti-cancer | NT Binding Assay |
|---|---|---|---|
| Cytoskeleton [a] | cis-platin | + | + |
|  | Taxol | + | + |
| Mitochondria [b] | antimycin A | + | + |
|  | rotenone | + | + |
|  | Gossypol | + | + |
| Glycolysis [c] | 2-deoxyglucose | + | + |
| Isoprenoids [d] | farnesol | + | + |
|  | Mevinolin | + | + |
| Retinoids [e] | retinoic acid | + | + |
| Lipoxygenases [f] | NDGA | + | + |
|  | MK886 | + | + |
|  | baicalein | + | + |
| tyrosine kinases [h] | genistein | + | + |
|  | AG1478 | + | + |
|  | Apigenin | + | + |
| VEGF | SU5416 | + | + |
| Protein kinase C [g] | bisindole maleimide | + | + |
|  | Go-6983 | + | + |
|  | Quercetin | + | + |
| PI3 kinase [i] | wortmannin | + | + |
| Glycogen synthase [j] Kinase | SB-216763 | + | + |
| DAG-lipase | RHC-80267 | + | + |
| ROS-scavenger | luteolin | + | + |
|  | resveratrol | + | + |
| flavoprotein oxidase | diphenylene iodonium | + | + |
| Fe/Zn chelator | o-phenanthroline | + | + |
| Estrogen receptor | diethylstilbesterol | + | + |
|  | Estradiol | + | + |
| Calcium channels [k] | nifedipine | + | + |
|  | Nicardipine | + | + |

[a] Loprevite et al., Int. J. Oncol., 15: 787-892, 1999.
[b] Jiang et al., Anticancer Res., 24: 91-100, 2004; Isenberg et al., Carcinogenesis, 18: 1511-1519, 1997.
[c] Liu et al., Biochemistry, 40: 5542-5547, 2001.
[d] Rao et al., Cancer Detect. Prev., 26: 419-425, 2002; Mo et al., Exp. Biol. Med., 229: 567-585, 2004.
[e] Keedwell et al., Br. J. Cancer, 91: 580-588, 2004; Bartolini et al., Anticancer Res., 34: 1779-1783, 2004.
[f] Matsuyama et al., Int. J. Oncol, 24: 821-827.
[g] Da Rocha et al., Oncologist, 7: 17-33, 2002.
[h] Shukla et al., Mol. Carcinog., 39: 114-126, 2004.
[i] Klaleghpour et al., Carcinogenesis, 25: 241-248, 2004.
[j] Fishman et al., Oncogene, 23: 2465-2471, 2004. Yoshida et al., Eur. J. Pharmacol., 472: 23-31; Jager et al., Mol. Pharmacol., 65: 630-638, 2004.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a candidate compound with antioxidant or antiproliferative activity, or both, the method comprising:
    contacting a test compound to a cell expressing neurotensin receptors on its cell surface;
    contacting the cell with a neurotensin receptor ligand;
    monitoring binding of the ligand to the cell; and
    selecting the test compound as a candidate compound with antioxidant or antiproliferative activity if the test compound enhances binding of the ligand to the cell, relative to binding of the ligand to a cell of the same cell type that is not contacted with the test compound.

2. The method of claim 1, wherein the test compound is a compound that belongs to a class selected from the group consisting of: dihydropyridines, polyphenols, flavonoids, isoprenoids, retinoids, inhibitors of mitochondrial function, inhibitors of glycolysis, inhibitors of glycogen synthase kinase, inhibitors of flavoprotein oxidases, iron/zinc chelators, inhibitors of lipoxygenases, inhibitors of protein kinase C, inhibitors of PI3-kinase, inhibitors of tyrosine kinases, and estrogen agonist.

3. The method of claim 1, wherein the ligand is neurotensin.

4. The method of claim 1, wherein the ligand is selected from the group consisting of neurotensin; a neurotensin fragment comprising neurotensin (8-13); neurotensin or an analog or fragment thereof with a substitution at one or more of the following positions: Arg 8, Arg 9, Pro 10, or Tyr 11, Ile 12, or Leu 13; a neurotensin with tryptophan substitution for Tyr 11; a neurotensin analog or fragment thereof MP-2530; Neuromedin-N; xenopsin; xenin; histamine releasing peptide; SR48692; SR142948A; and levocabastine.

5. The method of claim 1, wherein the ligand is radiolabeled.

6. The method of claim 1, wherein the cell is a cultured cell from a tumor selected from the group consisting of a Ewing's sarcoma, a myeloma, an astrocytoma, a lung tumor, a colon tumor, an ovarian tumor, a pancreatic tumor, and a prostate tumor.

7. The method of claim 1, further comprising:
contacting a cancer cell with the selected candidate compound;
monitoring proliferation of the cancer cell; and
identifying the candidate compound as an antiproliferative agent if the candidate compound inhibits proliferation of the cancer cell relative to proliferation of a cancer cell of the same cell type that is not contacted with the candidate compound.

8. The method of claim 7, wherein the cancer cell is a cell selected from the group consisting of a Ewing's sarcoma cell, a myeloma cell, an astrocytoma cell, a lung tumor cell, a colon tumor cell, an ovarian tumor cell, a pancreatic tumor cell, and a prostate tumor cell.

9. The method of claim 1, wherein the method is repeated for a plurality of test compounds.

10. The method of claim 1, wherein the cell is selected from the group consisting of a Ewing's sarcoma cell, a myeloma cell, an astrocytoma cell, a lung tumor cell, a colon tumor cell, an ovarian tumor cell, a pancreatic tumor cell, and a prostate tumor cell.

11. The method of claim 1, wherein the test compound is selected as a candidate compound with antiproliferative activity if the test compound enhances binding of the ligand to the cell, relative to binding of the ligand to a cell of the same cell type that is not contacted with the test compound.

12. The method of claim 11, wherein the test compound is a compound that belongs to a class selected from the group consisting of: dihydropyridines, polyphenols, flavonoids, isoprenoids, retinoids, inhibitors of mitochondrial function, inhibitors of glycolysis, inhibitors of glycogen synthase kinase, inhibitors of flavoprotein oxidases, iron/zinc chelators, inhibitors of lipoxygenases, inhibitors of protein kinase C, inhibitors of PI3-kinase, inhibitors of tyrosine kinases, and estrogen agonist.

13. The method of claim 11, wherein the ligand is neurotensin.

14. The method of claim 11, wherein the ligand is selected from the group consisting of neurotensin; a neurotensin fragment comprising neurotensin (8-13); neurotensin or an analog or fragment thereof with a substitution at one or more of the following positions: Arg 8, Arg 9, Pro 10, or Tyr 11, Ile 12, or Leu 13; a neurotensin with tryptophan substitution for Tyr 11; a neurotensin analog or fragment thereof MP-2530; Neuromedin-N; xenopsin; xenin; histamine releasing peptide; SR48692; SR142948A; and levocabastine.

15. The method of claim 11, wherein the ligand is radiolabeled.

16. The method of claim 11, wherein the cell is a cultured cell from a tumor selected from the group consisting of a Ewing's sarcoma, a myeloma, an astrocytoma, a lung tumor, a colon tumor, an ovarian tumor, a pancreatic tumor, and a prostate tumor.

* * * * *

UNITED STATES PATENT AND TRADEMARK OFFICE
CERTIFICATE OF CORRECTION

PATENT NO. : 7,507,547 B2  Page 1 of 1
APPLICATION NO. : 11/223395
DATED : March 24, 2009
INVENTOR(S) : Robert E. Carraway It is certified that error appears in the above-identified patent and that said Letters Patent is hereby corrected as shown below:

Title page, item (56), column 2, line 25 under Cochrane et al., replace "activities" with --activity--.

Column 41, line 5, after "thereof" insert --;--.

Column 42, line 23, after "thereof" insert --;--.

Signed and Sealed this

Twenty-third Day of June, 2009

JOHN DOLL
*Acting Director of the United States Patent and Trademark Office*